United States Patent [19]

Zhang

[11] Patent Number: 5,767,276

[45] Date of Patent: Jun. 16, 1998

[54] ASYMMETRIC SYNTHESIS CATALYZED BY TRANSITION METAL COMPLEXES WITH NEW CHIRAL LIGANDS

[75] Inventor: Xumu Zhang, State College, Pa.

[73] Assignee: The Penn State Research Foundation, University Park, Pa.

[21] Appl. No.: 729,469

[22] Filed: Oct. 11, 1996

Related U.S. Application Data

[60] Provisional application No. 60/005,196 Oct. 13, 1995 and provisional application no. 60/006,858 Nov. 16, 1995.

[51] Int. Cl.[6] .............................. C07F 9/80; C07F 9/06; C07F 9/02
[52] U.S. Cl. ..................... 546/2; 546/22; 568/8; 568/13
[58] Field of Search ............................ 546/2, 22; 568/8, 568/13

[56] References Cited

U.S. PATENT DOCUMENTS

| | | |
|---|---|---|
| 4,124,533 | 11/1978 | Knowles et al. |
| 4,142,992 | 3/1979 | Knowles et al. |
| 4,331,818 | 5/1982 | Riley |
| 4,694,094 | 9/1987 | Juge et al. |
| 4,879,008 | 11/1989 | Puckette |
| 4,952,740 | 8/1990 | Juge et al. |
| 4,954,227 | 9/1990 | Puckette |
| 4,956,055 | 9/1990 | Puckette |
| 5,026,886 | 6/1991 | Stavinoha et al. |
| 5,264,602 | 11/1993 | Juge et al. |
| 5,434,285 | 7/1995 | Laffitte et al. |

OTHER PUBLICATIONS

Gorla et al., Organemetallics, 1994, vol. 13 pp. 43–54.

*Primary Examiner*—Deborah Lambkin
*Attorney, Agent, or Firm*—Thomas J. Monahan

[57] ABSTRACT

A chiral ligand having the following structure:

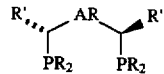

wherein AR is any aromatic and/or ring structure, and R is selected from the group consisting of aryl, oxygenated aryl, alkyl, oxygenated alkyl, AR, oxygenated AR and combinations thereof.

35 Claims, 10 Drawing Sheets

R, R' = aryl, alkyl groups

DIOP　　　　　　　Chiraphos　　　　　　　Binap

X, Y, Z = Substituent on pyridine ring; e.g., NMe$_2$, OMe, Me, H, F, Cl, Br, NO$_2$ R, R$_1$, R$_2$ = Alkyl and aryl and other substituents; e.g., Me, Et, $^i$Pr, $^t$Bu, Ph, OR, OAr; n = 1, 2, 3.

S to Z = Substituent on aromatic groups; e.g., NMe$_2$, OMe, Me, H, F, Cl, Br, NO$_2$ R, R' = alkyl and aryl and other substituents; e.g., Me, Et, $^i$Pr, $^t$Bu, Ph, OR, OAr

ASYMMETRIC SYNTHESIS CATALYZED BY TRANSITION METAL COMPLEXES WITH NEW CHIRAL LIGANDS

FIELD OF THE INVENTION

This application claims priority from both Provisional application Ser. No. 60/005,196, filed Oct. 13, 1995 and Provisional application Ser. No. 60/006,858, filed Nov. 16, 1995. The present invention relates to chiral ligands useful in asymmetric synthesis catalysts. More particularly, the present invention relates to new bidentate and tridentate, chiral phosphine ligands providing high selectivity of the enantiomeric structure of the end-product.

BACKGROUND OF THE INVENTION

Molecular chirality plays a very important role in science and technology. The biological activities of many pharmaceuticals, fragrances, food additives and agrochemicals are associated with their absolute molecular configuration. Furthermore, the physical properties of some electronic and optical devices also depend on their molecular asymmetry. Thus, the efficient creation of enantiomerically pure molecules can have a profound impact on diverse areas of science and technology. To meet this challenge, chemists have explored many approaches for acquiring enantiomerically pure compounds, ranging from optical resolution and structural modification of naturally occurring chiral substances to asymmetric catalysis using synthetic chiral catalysts and enzymes.

Among these methods, asymmetric catalysis is perhaps the most efficient because a small amount of a chiral catalyst can be used to produce a large quantity of a chiral target molecule. During the last two decades, great attention has been devoted to discovering new asymmetric catalysts. More than a half-dozen commercial industrial processes have used asymmetric catalysis as the key step in the production of enantiomerically pure compounds.

Many successful transition metal mediated catalytic asymmetric reactions utilize functionalized substrates. These substrates have ligating groups which participate in secondary interactions between the substrate and the transition metal center. Such secondary interactions constrain the orientation of the substrate in the transition state and facilitate enantiodifferentiation in asymmetric reactions.

In comparison, enantioselective catalytic reactions with unfunctionalized substrates are more difficult to achieve and remain as great challenges because selectivity can only rely on relatively diffuse non-bonding interactions between the catalyst and the substrate. So far, there are only a few efficient catalytic systems reported in the literature which describe asymmetric catalysis with unfunctionalized substrates. Certain chiral phosphine ligands have been successfully used to mediate catalytic asymmetric reactions.

This invention discloses newly developed transition metal complexes with chiral ligands that catalyze asymmetric reactions of unfunctionalized substrates (ketones, imines, olefins, aldehydes, etc.). These ligands can be bidentate or tridentate. A variety of asymmetric reactions such as hydrogenation, hydride transfer reaction, hydrosilylation, hydroboration, hydroformylation, hydrocyanation, hydrocarboxylation, allylic alkylation, cyclopropanation, Diels-Alder reaction, Aldol reaction and Michael addition can be catalyzed by means of these innovative ligand systems. The success of this approach can lead to efficient and practical methods for producing important chiral drugs for antihypertensive, antihistamine, cardiovascular and central nervous system therapies, among others.

Various $C_2$ symmetric bidentate phosphines have been reported in the literature. For example, the Diop and Chirophos ligands have been made for asymmetric hydrogenation. The backbone of Diop has two methylene groups and is very flexible. This flexibility limits its enantiomeric selectivity. Chirophos coordinates with metals in a five membered ring and the bite angle it forms is not very large. This bite angle size limitation limits the efficiency with which this ligand can catalyze the asymmetric hydrogenation reaction. The Binap, another such ligand and perhaps the most effective of the three, forms a conformationally unambiguous seven-membered chelate ring with transition metals. However, the rotation of its aryl-aryl bond makes the Binap very flexible. This flexibility is an inherent limitation. In addition, because the Binap phosphine contains three aryl groups, it is less electron donating than phosphines that have two aryl groups and one alkyl group. A few tridentate ligands such as Pythia and Pybox have also been disclosed for use in certain reactions.

Thus, the present inventor has discovered a class of unique chiral phosphine ligands that are capable of providing high selectivity of the enantiomeric structure of the end-products formed from the asymmetric reactions such as hydrogenation, hydride transfer reaction, hydrosilylation, hydroboration, hydroformylation, hydrocyanation, hydrocarboxylation, allylic alkylation, cyclopropanation, Diels-Alder reaction, Aldol reaction and Michael addition.

The ligands of the present invention are suitable for catalyzing asymmetric reactions of unfunctionalized substrates that provides superior efficiency and conversion rates. Moreover, these unique ligands are also suitable for catalyzing asymmetric reactions due to their rigid bite angle that facilitates enantioselective catalysis.

SUMMARY OF THE INVENTION

Accordingly, the present invention is generally directed to a novel chiral ligand having the following structure:

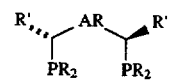

wherein AR is any aromatic and/or ring structure, and R is selected from the group consisting of aryl, alkyl, aralkyl, ring-substituted aralkyl, substituted aryl and combinations thereof Ar can be, without limitation, aryl, divalent aryl, divalent fused heterocyclic group, heteroaryl, or substituted aryl, wherein the substitution of aryl can be independently selected from, without limitation, hydrogen, halogen, alkyl, alkoxyl, aryl, aryloxy, nitro, amino, vinyl, substituted vinyl, alkynyl or sulfonic acids. The substitution of R can be, without limitation, hydrogen, halogen, alkyl, aryloxy, nitro, amino, vinyl, substituted vinyl, alkynyl or sulfonic acids. This unique ligand can preferably be any one structure selected from the group consisting of:

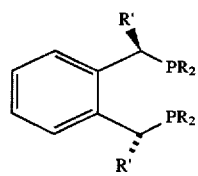

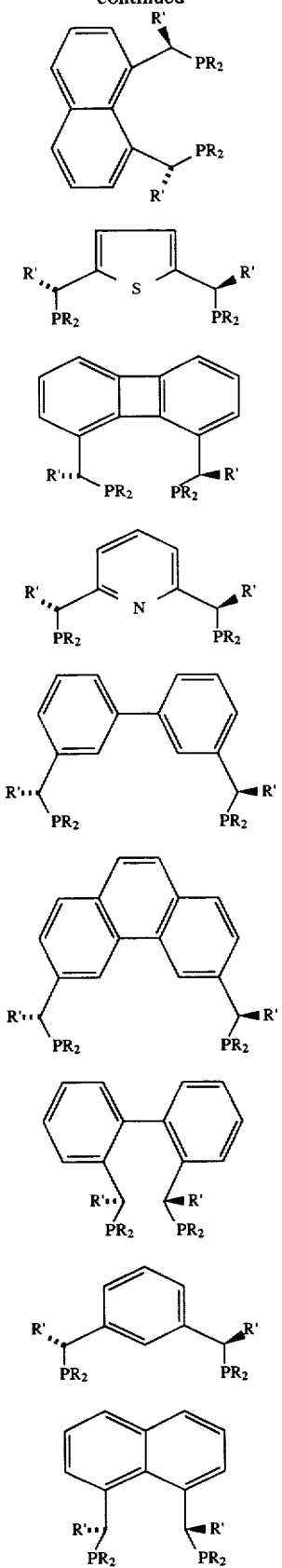
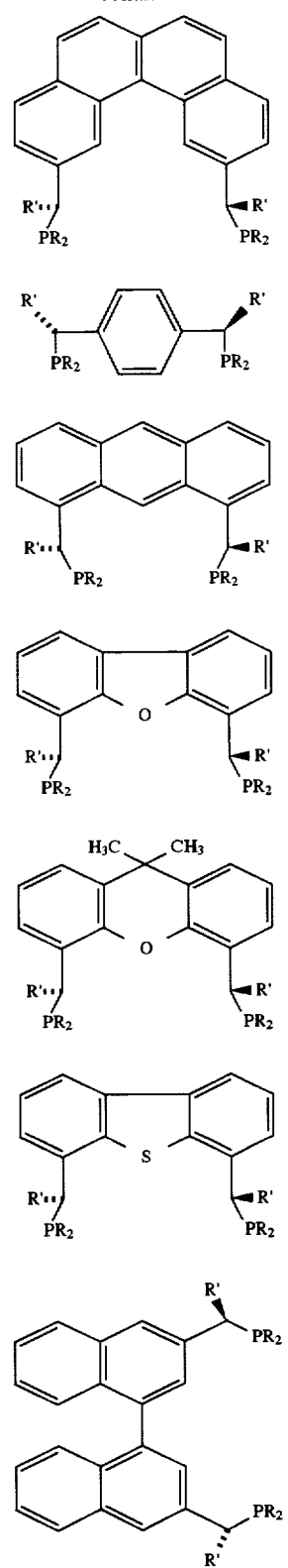

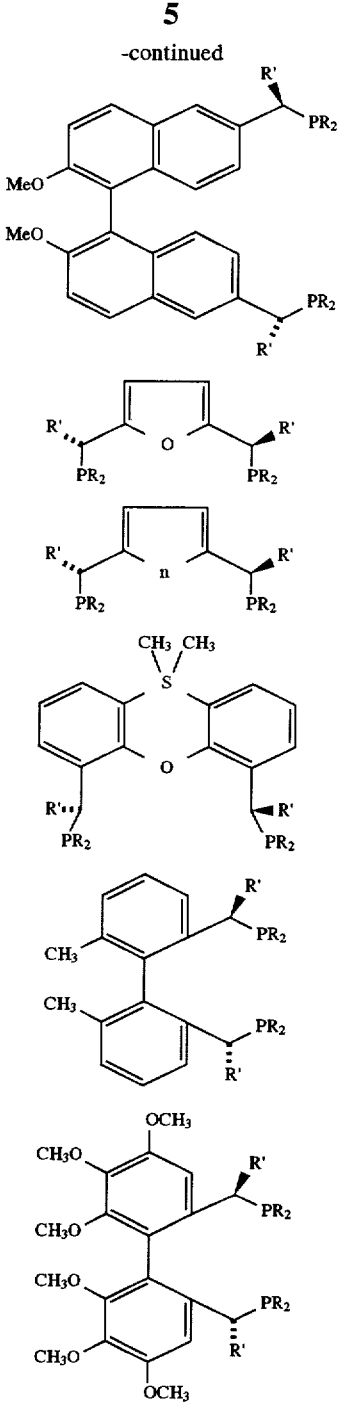

wherein Me is CH₃ and n is NH.

The substituents about the aromatic and/or ring structure (AR) are preferably selected from the group consisting of: $N(CH_3)_2$, $OCH_3$, $CH_3$, hydrogen, fluorine, chlorine, bromine and $NO_2$.

The present invention is also directed to a catalyst which comprises:

a transition metal; and a chiral ligand having the following structure:

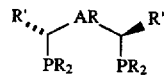

wherein AR is any aromatic and/or ring structure, and R is selected from the group consisting of aryl, alkyl, aralkyl, ring-substituted aralkyl, substituted aryl and combinations thereof. The transition metal is preferably at least one metal selected from Group VIII metal, e.g., rhodium, iridium, ruthenium and palladium.

The unique catalyst formed in accordance with the present invention can be used to enhance the selectivity of a variety of asymmetric reactions such as hydrogenation, hydride transfer reaction, hydrosilylation, hydroboration, hydroformylation, hydrocyanation, hydrocarboxylation, allylic alkylation, cyclopropanation, Diels-Alder reaction, Aldol reaction and Michael addition.

The present invention also relates to chiral ligands having the following structure:

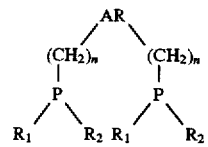

wherein AR is any aromatic and/or ring structure, $R_1$ and $R_2$ are different and are selected from the group consisting of aryl, alkyl, aralkyl, ring-substituted aralkyl, substituted aryl and combinations thereof, and n=1 or 2.

DESCRIPTION OF THE PREFERRED EMBODIMENTS

The present invention discloses, in part, various phosphine ligands with aromatic backbones (see FIG. 1) Some of these ligands, in bidentate form, surpass the Binap and other known bidentate ligands (see FIG. 2) in performance. FIG.

3 shows the calculated structure of a metal-Binap complex and of a metal complex with one ligand as disclosed in the patent. While the two complexes have similar structure overall, the two equatorial phenyls protrude more from P-M-P than the corresponding phenyls of Binap. This is due to the fact that the bite angle of the ligand of the present invention is greater than that of Binap.

Figure 4:
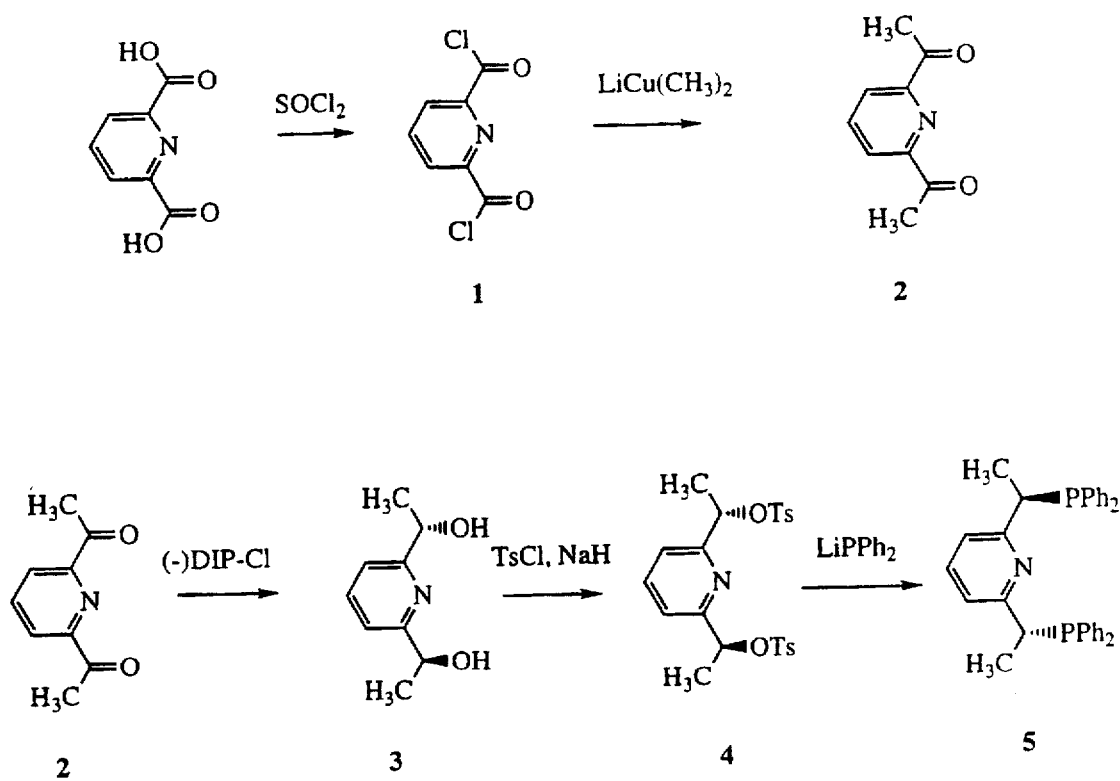
FIG. 4 depicts a representative synthesis pathway.

The chiral ligands of the present invention also contain fewer aryl groups than Binap, and can donate more electrons to metal than Binap. This allows the ligands of the present invention to accelerate many of the relevant reactions. Compared to Diop, Chirophos and Binap, the new chiral bidentate phosphines have a rigid backbone, and the bite angles can be adjusted by changing ring size (80° to 180°). A common feature of these ligands is that they also have unambiguous chelate configuration with transition metals. Instead of having a flexible ligand like Binap to adopt the coordination requirements of transition metals through axial rotation, these ligands can force the transition metals to accept certain coordination requirements. Thus, a higher enantioselectivity can be achieved when ligands are employed in the appropriate reactions to be catalyzed. One representative efficient synthesis pathway is shown in FIG. 4. These powerful ligands are suitable for a variety of asymmetric reactions.

Figure 1:
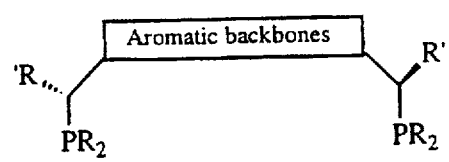
FIG. 1 is a schematic depiction of the ligands of the present invention.
Figure 2:
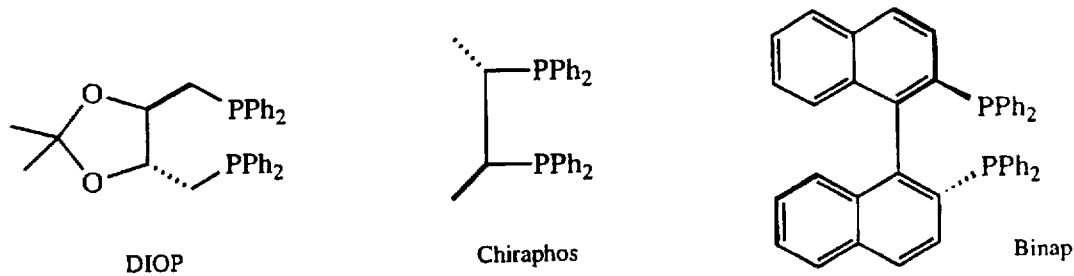
FIG. 2 depicts several prior art bidentate phosphine ligands.
Figure 3:
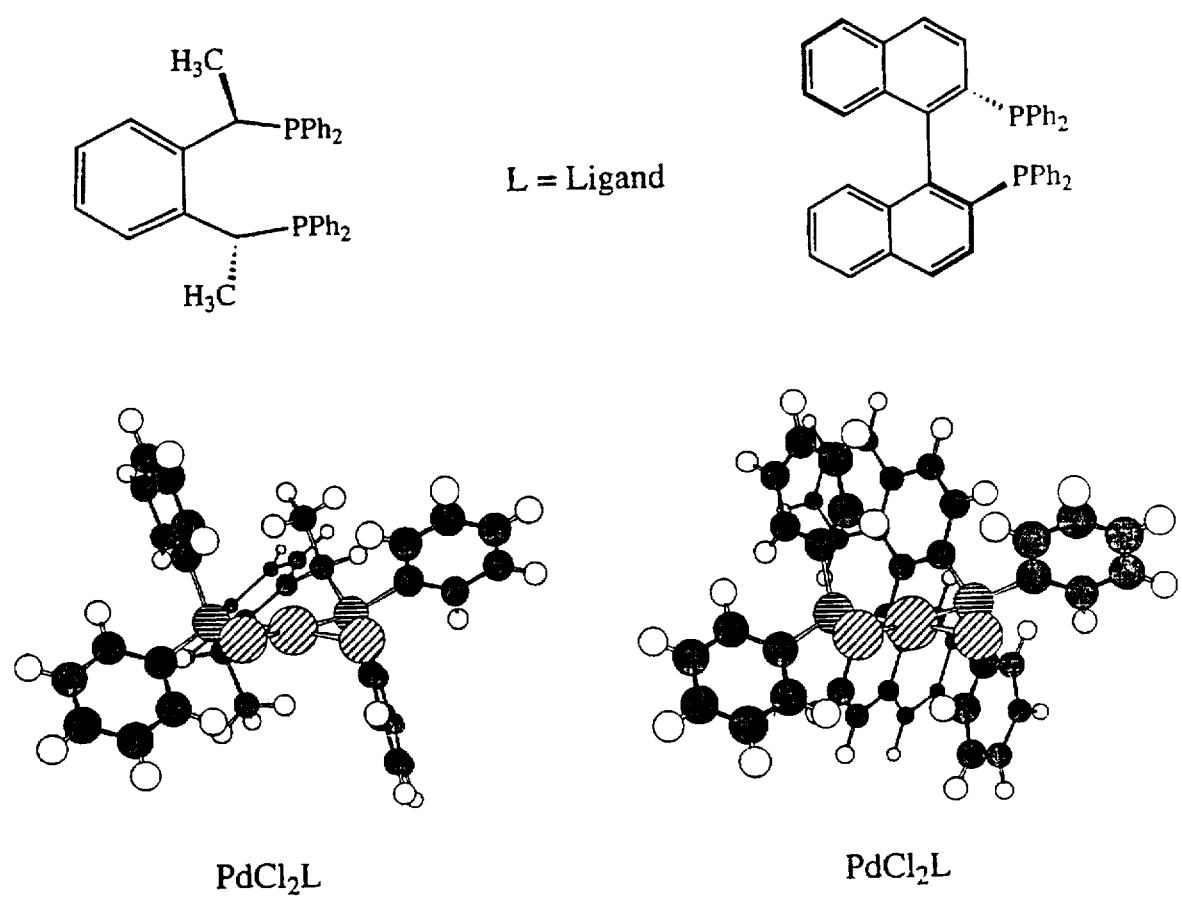
FIG. 3 contrasts the Binap bidentate ligand with a representative bidentate ligand of the present invention.

The present invention discloses the family of ligands with two chiral phosphine groups and aromatic backbones, as shown in FIG. 1. As discussed above, with aromatic backbones in the center, these ligands have a rigid structure. Depending on the aromatic groups, bidentate or multidentate ligands can result. For example, in a preferred embodiment, a center pyridine can be used to form tridentate ligands having one nitrogen and two phosphine ligands. In more general situations, many other aromatic backbones can be used.

Figure 5:
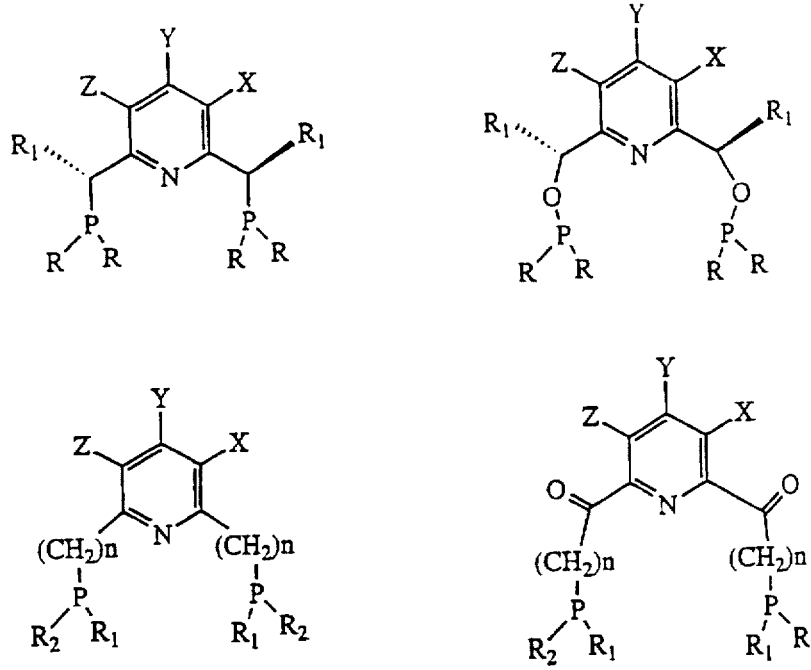
FIG. 5 depicts representative tridentate ligands of the present invention.
Figure 5:
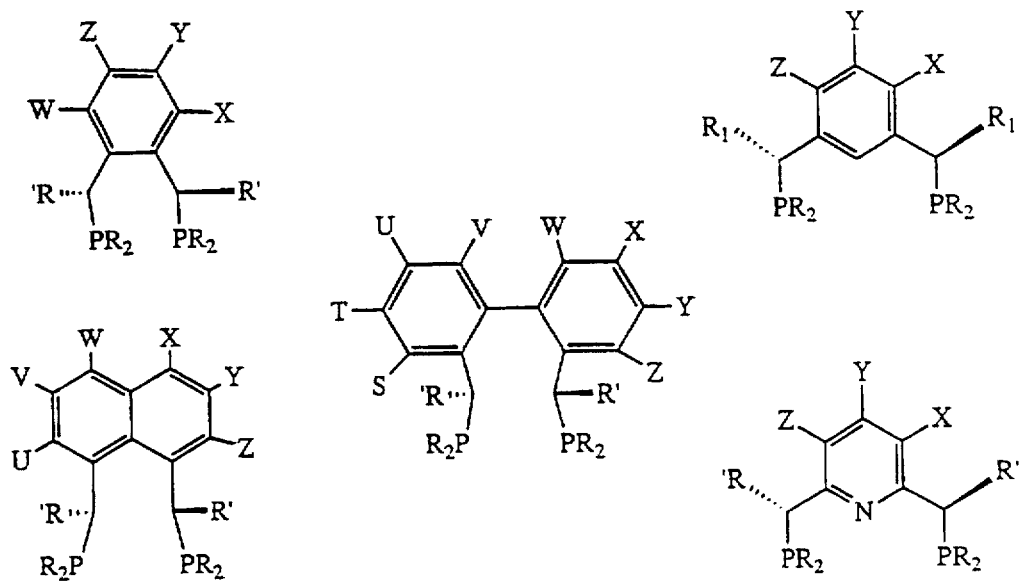

Thus, the present invention discloses chiral ligands such as the tridentate ligands having the structures shown in FIG. 5. Group VIII transition metal complexes formed with these ligands are used to facilitate a variety of catalytic reactions. These representative ligands have diverse electronic properties as a consequence of the range of phosphorus ligands used (alkyl phosphines, arylphosphines, phosphites). The steric environments also differ dramatically.

Figure 6:
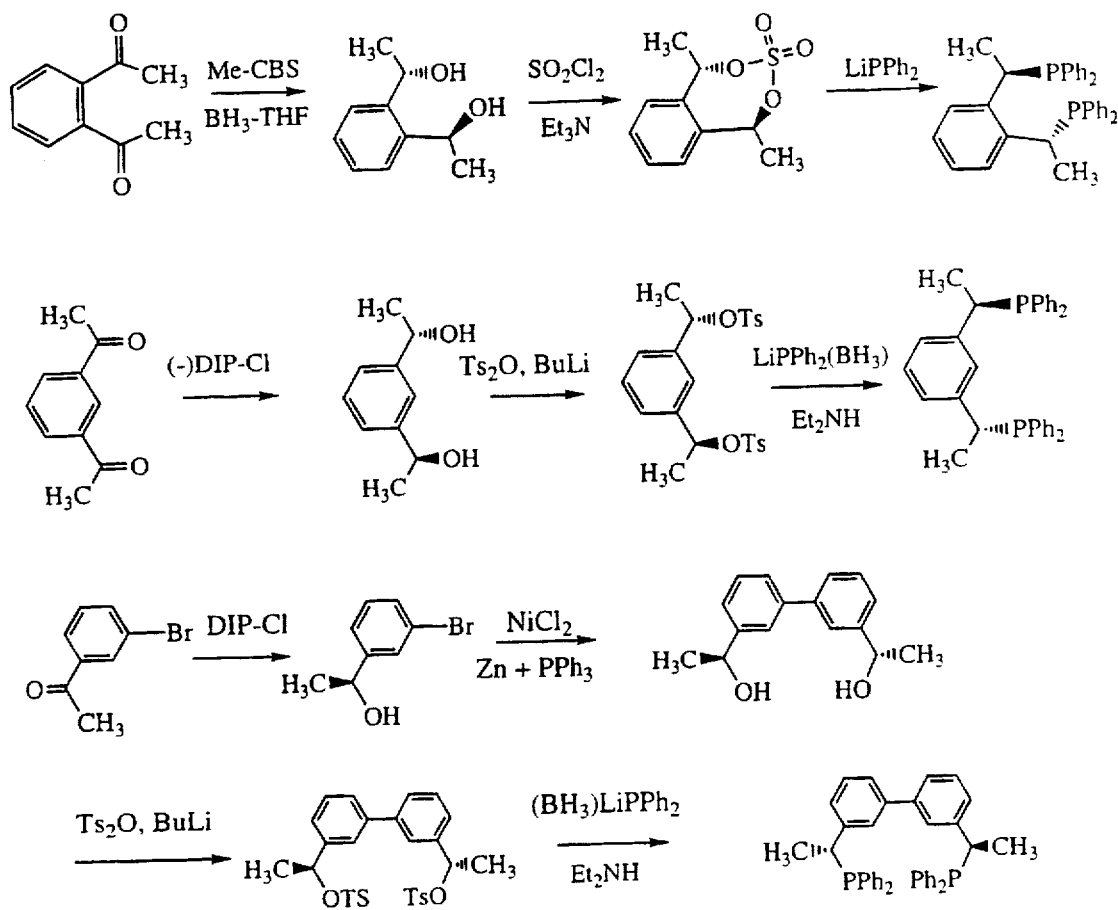
FIG. 6 depicts the derivation of chiral phosphines from optically pure aromatic diols.

FIG. 6 shows several chiral phosphines made from optically pure aromatic diols. (See also Examples 35 and 36, below). There are several key steps for the synthesis of chiral ligand I. Probably the most difficult step is the synthesis of the optically pure 1,4-diol. This simple chiral diol has not been synthesized before. We have obtained the chiral diol in gram scale with 100% ee through reduction of borane with Me-CBS reagent as catalyst. The cyclic sulfate was made. Nucleophilic attack by diphenylphosphine anion gives the desired Benphos ligand in high yield.

The ligand 2 has chiral carbon with a benzene ring in 1,3-position. The diketone is reduced to chiral alcohol by Dip-Cl. Tosylation with $Ts_2O$ in situ at a low temperature and nucleophilic addition with borane protected $LiPPh_2$ produce the ligand 2 with borane protection. Deprotection with $Et_2NH$ gives the product 2 in high yield.

Ligand 3 is a trans chiral phosphine. The strategy for the ligand synthesis involves asymmetric reduction of 3-bromoacetophenone with Dip-Cl, Ni-catalyzed coupling reaction, tosylation and nucleophilic addition of $LiPPh_2$ ($BH_3$). Tosylate of benzyl alcohols are generally not stable and can only be produced in situ at a low temperature using the method in FIG. 6 ($Ts_2O$+BuLi). It was found that a strong base (BuLi or $LiPPh_2$) will racemize the chiral center adjacent to the phosphine by removing the benzyl proton in some cases. Addition of protected phosphine with $BH_3$ decreases the basicity of —$PPh_2$ and no racemization is observed. Deprotection of $BH_3$ from phosphine with nitrogen base gives the product. This is the preferred method for deriving ligands according to the present invention.

This invention also discloses a practical way of preparing 2,6-diketopyridine (see FIG. 4) by a coupling reaction between acid chloride and cuprates. Furthermore, asymmetric reduction with chiral borane reducing agents is a key step in the ligand preparation. The detailed procedures are described in the example section, below.

Thus, a most preferred family of ligands with two chiral phosphine groups in trans positions is disclosed herein to promote enantioselective reactions of unfunctionalized substrates (see, e.g., FIGS. 1 and 5). The tridentate ligands with a pyridine nitrogen atom in the center of this family of ligands generally binds transition metals in a planar geometry and creates a well defined chiral environment for catalytic reactions. Transition metals such as Rh(I), Ir(I), Pd(II) and Ru(II) will be used in these complexes due to their high activity in a variety of catalytic reactions such as hydrogenation, hydroformylation and allylic alkylation.

Figure 7:
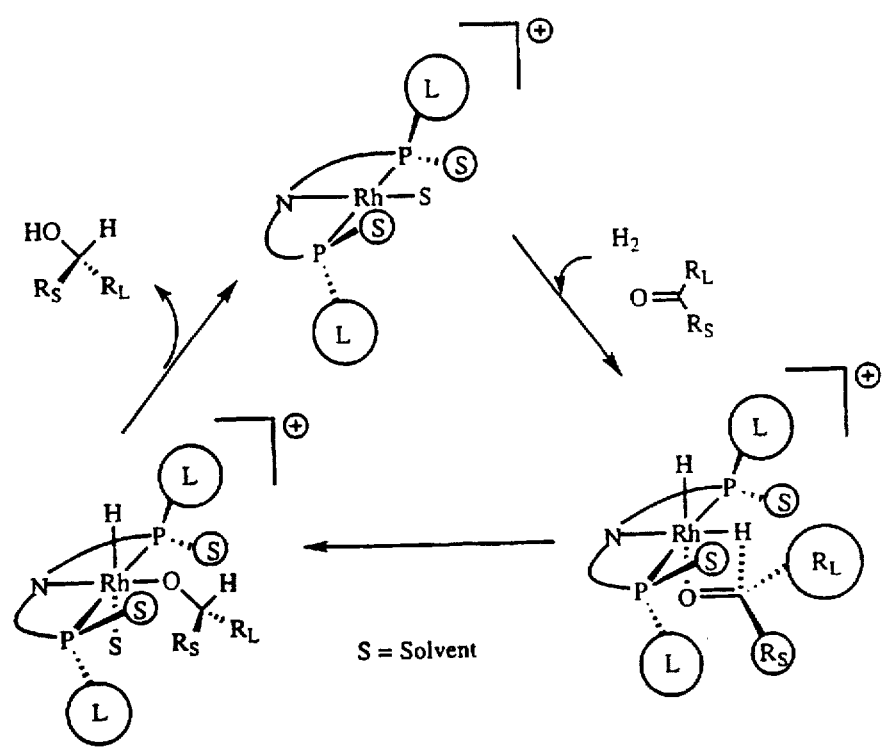
FIG. 7 depicts the hydrogenation of ketones by means of a ligand according to the present invention.

This tridentate ligand system offers certain advantages in controlling the selectivity of certain reactions versus known chiral $C_2$ symmetric bidentate ligands. To illustrate this point, an example featuring asymmetric hydrogenation of unfunctionalized ketones is shown in FIG. 7. Two possible transition state assemblies with bidentate and tridentate ligands are described. In FIG. 7 the ketone is far away from the bidentate ligand and very little non-bonding interaction exists between the substrate and the chiral phosphine ligand. This analysis is in good agreement with the fact that only moderate enantioselectivities (8–80% enantiomeric excess, or "ee") have been observed in a hydrogenation reaction when known chiral bidentate phosphines were used as the ligands. On the other hand, the tridentate ligand shown in FIG. 7 could effectively discriminate between the two enantiotopic approaches of a ketone through more pronounced interactions between the catalyst and the substrate. As a consequence, high enantioselectivity is obtained in this context. Strong support for this theory stems from the observation that a $C_2$ symmetric tridentate ligand (2,6-bisoxazolidinylpyridine) has been successfully used in asymmetric hydrosilylation of unfunctionalized ketones. However, this ligand binds with three nitrogen atoms and could not provide the required electronic properties for other catalytic reactions. Because phosphine ligands are commonly used in homogenous catalysis, it is more desirable to introduce chiral tridentate ligands with several types of phosphine atoms to facilitate various catalytic reactions. It must be noted, however, that the functionality of these ligands is highly context-specific.

Figure 8:
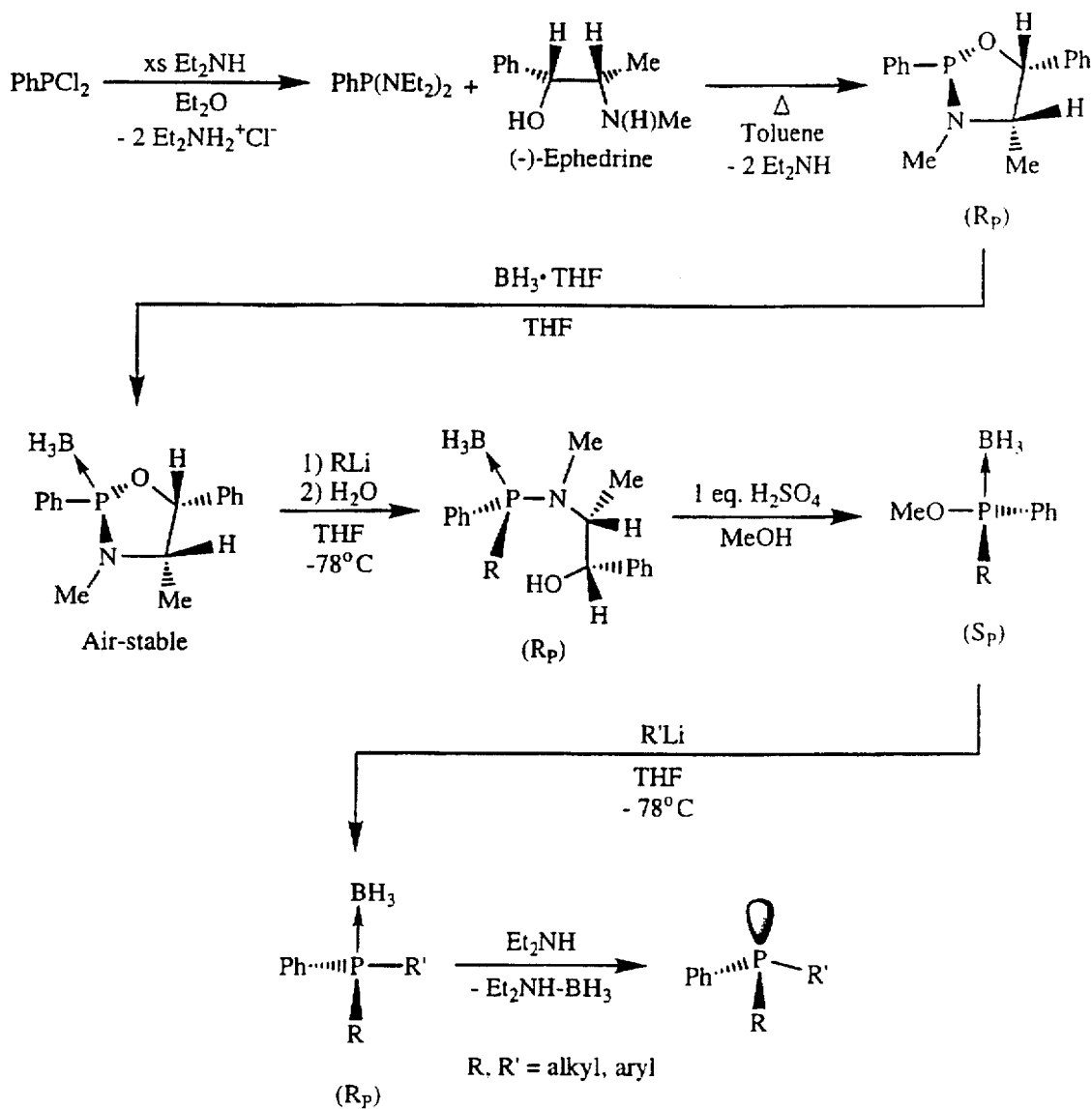
FIG. 8 depicts a reported procedure used to synthesize chiral scalemic phosphines.
Figure 9:
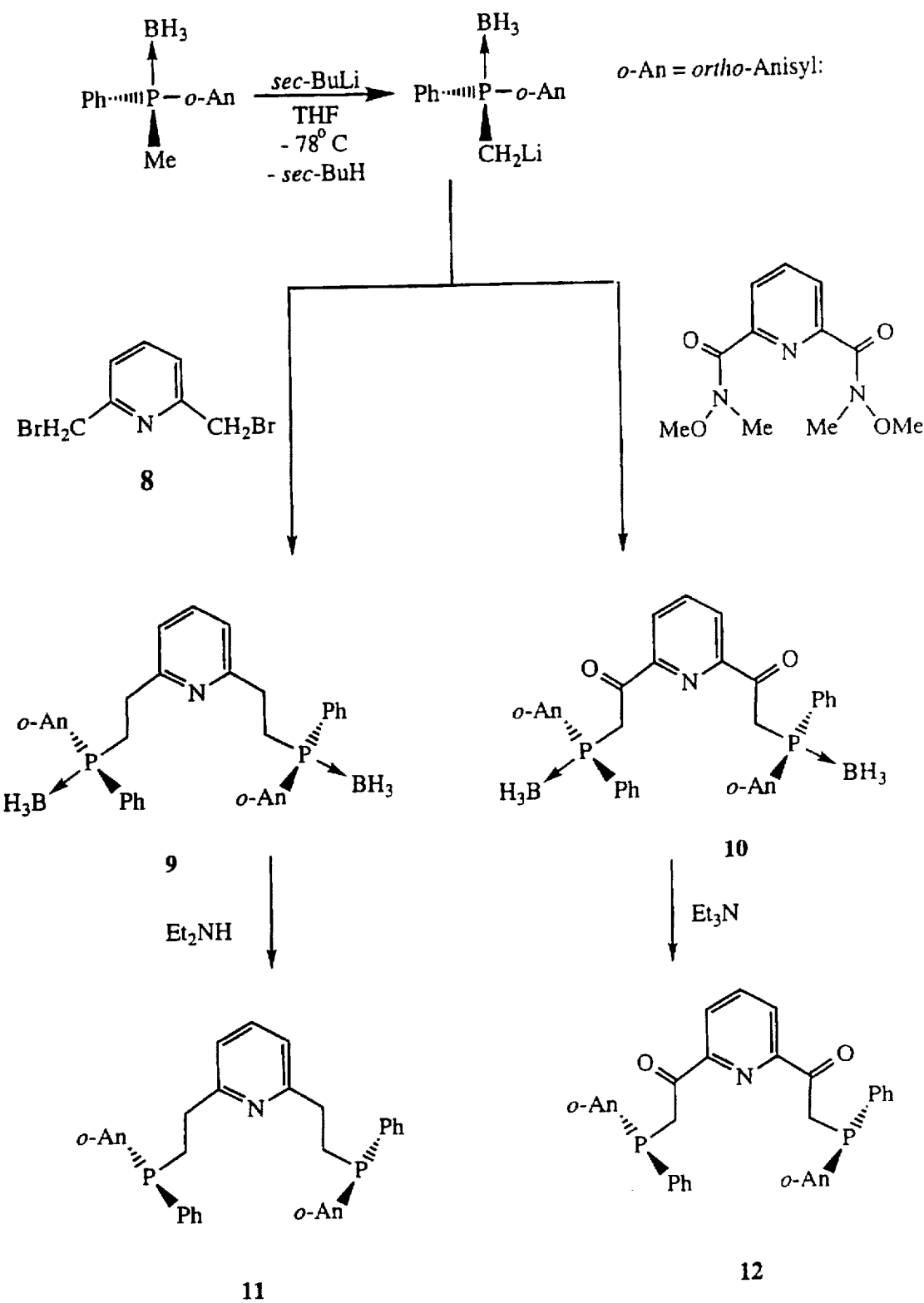
FIG. 9 depicts the addition of pyridines to produce preferred ligands of the present invention.
Figure 10:
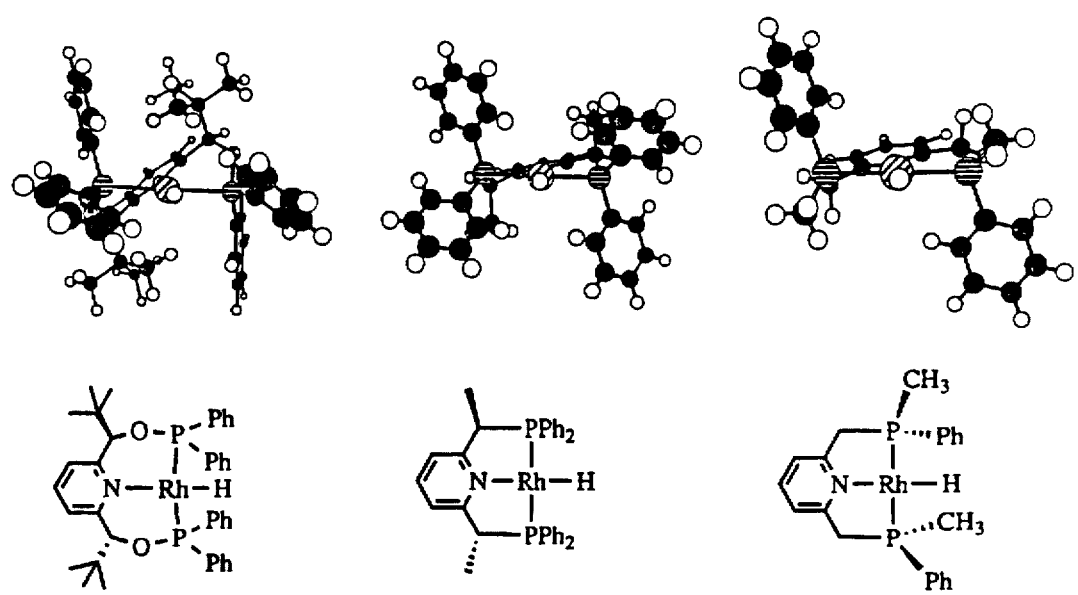
FIG. 10 depicts the typical coordination geometries of RhH(L)

As discussed above, asymmetric reduction with chiral borane reducing agents is a key step in the ligand preparation. The detailed procedures are described in the examples, below. A reported preparation procedure is used to synthesize chiral scalemic phosphine, as shown in FIG. 8. Coupling the scalemic phosphine with various pyridines generates chiral tridentate ligands (FIG. 9). In a similar manner, chiral bidentate ligands according to the present invention, containing nitrogen and phosphine, can be synthesized. To demonstrate that these ligands fit the required geometry for asymmetric reactions, molecular modeling studies based on a CAChe program were carried out. FIG. 10 shows the typical coordination geometries of RhH(L) (L=tridentate ligands). The first two ligands have two sets of phenyl groups. Two equatorial phenyl groups protrude to the P—Rh—P in-plane coordination sites and two axial phenyls stay back. These two equatorial phenyl groups are regarded as large groups in the designed chiral tridentate ligand system. The third ligand has a methyl group and a phenyl group. The methyl group is smaller than phenyl group in the configuration.

A variety of asymmetric reactions employing the family of chiral ligands of the present invention are set forth below. Many other reactions such as asymmetric hydride transfer reaction, hydrosilylation, hydroformylation, hydrocarboxylation, hydrocyanation, and hydroboration follow a pattern pathway similar to that of the hydrogenation reaction and can be pursued in an analogous manner. Asymmetric carbon-carbon bond forming reactions can also be catalyzed with these tridentate ligands. Such reactions include allylic alkylation, cycloproparation, aldol reactions, Diels-Alder reactions and Michael addition reactions. Group VIII transition metal complexes are excellent catalysts for these reactions and have been used in large scale syntheses of important industrial products. Efficient asymmetric catalysts for these reactions can be achieved with the chiral tridentate ligands disclosed herein.

EXAMPLES OF LIGAND FORMATION

Example 1

Preparation of Bis(diethylamino)phenylphosphine [PhP(NEt$_2$)$_2$] (1).

Dichlorophenylphosphine (PhPCl$_2$; 50 g, 0.28 Mol, 37.9 mL) was added via syringe to a flame-dried 2 L, three-necked round-bottomed flask equipped with a large magnetic stir bar, 200 mL addition funnel, gas inlet adapter and septum. Freshly-distilled ether (approximately 1.5 L) was then added via cannula and the mixture cooled to 0° C. In a separate flask, diethylamine (Et$_2$NH; 4.5 equiv., 1.26 Mol, 91.9 g, 130 mL-vacuum transferred from MgSO$_4$ and degassed by three freeze-pump-thaw cycles) was diluted with 200 mL freshly-distilled ether and the solution transferred to the addition funnel via cannula. The amine solution was added dropwise to the phosphine mixture (maintained at 0° C.) over approximately 2 hours, resulting in the formation of a large quantity of insoluble Et$_2$NH$_2$$^+$Cl$^-$. When the addition of the Et$_2$NH solution was complete, the reaction mixture was allowed to warm to room temperature and stirred overnight. The mixture was then filtered (200 mL Schlenk frit) through a 1" plug of Celite using a largebore Teflon tube as a cannula, and the colorless filtrate collected in a flame-dried 2 L Schlenk round-bottomed flask. Note: Due to the large quantity of Et$_2$NH$_2$$^+$Cl$^-$, two Schlenk frits were required. When a frit became filled, the salt was washed thoroughly with freshly-distilled ether and then the frit replaced. Removal of the volatiles from the filtrate under reduced pressure afforded crude PhP(NEt$_2$)$_2$ as a pale yellow oil. Approximately 5 mL silicone oil was added to the oil and the mixture distilled through a 10 cm Vigreux column under vacuum. The mixture was heated to approximately 160° C. and PhP(NEt$_2$)$_2$ (1) distilled at a head temperature of 110° C. and was obtained as a colorless liquid (67.6 g, 0.27 Mol, 96% yield).

1: $^1$H NMR (CDCl$_3$): δ7.5–7.3 (m, 5H, Ph); δ3.2–3.1 (dm, 8H, N(CH$_2$CH$_3$)); δ1.2 (tJ$_{HH}$=7.0 Hz, 12H, N(CH$_2$CH$_3$)).

Examples 2 and 3
Preparation of (2R,4S,5R)-2,5-Diphenyl-3,4-dimethyloxazaphospholidene borane

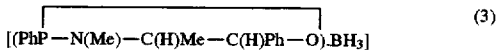
(3)

Bis(diethylamino)phenylphosphine (PhP(NEt$_2$)$_2$ (1); 37.1 g, 0.15 Mol) was dissolved in approximately 200 mL freshly-distilled toluene. In a separate flask, (−)-ephedrine (24.3 g, 0.15 Mol) was thoroughly degassed and dried under vacuum with gentle heating over 1 hour and then dissolved in approximately 250 mL toluene. The solution of 1 was then added to the ephedrine solution via cannula and the resulting mixture heated to 100°–105° C. overnight under nitrogen with vigorous stirring. The pale yellow solution was then cooled to room temperature and concentrated to approximately 150 mL under reduced pressure. Upon standing at room temperature, a large crop of white crystals of (2R,4S,5R)-2,5-diphenyl-3,4-dimethyloxazaphospholidene

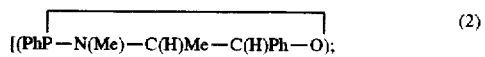
(2)

formed, and the mixture was then cooled to 0° C. for one hour to facilitate further crystallization. The colorless mother liquor was removed by means of a cannula tipped with filter paper and wrapped with PTFE tape and collected in a separate flame-dried Schlenk flask. The crystals were washed with hexane (2×20 mL) and the washings removed via cannula-filter and added to the collected mother liquor. The crystals were thoroughly dried under vacuum, affording pure 2 (25 g). The combined mother liquor/washings were concentrated to approximately 100 mL under reduced pressure and the solution stored overnight at −20° C., affording a second crop of crystalline 2. The mother liquor was removed via cannula-filter as above and retained in a separate flask, the crystals washed with hexane (2×15 mL), and the washings added to the collected mother liquor. Further concentration of the mother liquor/washings and dilution with hexane followed by storage at −20° C. resulted in the formation of additional crops of crystalline 2. The latter 2 crops of crystals were combined and recrystallized by dissolution of the solid in a minimal amount of ether with gentle heating, dilution of the solution with hexane and storage at −20° C. overnight. The mother liquor was removed via cannula and discarded, and the crystals washed with hexane (2×10 mL) and dried thoroughly under vacuum. All crops of crystalline material were combined in an inert-atmosphere glove box, affording 2 (32 g, 0.12 Mol, 80% yield).

In an inert-atmosphere glove box, 2 (15 g, 55.3 mmol) was placed in a flame-dried Schlenk flask. The flask was then equipped with an addition funnel and the system evacuated for 30 min. and then backfilled with nitrogen. Dry, degassed CH$_2$Cl$_2$ (approximately 100 mL) was added via cannula and the solution cooled to 0° C. BH$_3$·THF [1.1 equiv., 60.8 mmol, 60.8 mL (1.0M in THF] was then added dropwise over approximately 45 min. and the mixture stirred overnight and allowed to warm to room temperature. Removal of the volatiles from the mixture under reduced pressure afforded a white crystalline residue which was redissolved in a minimal amount of 1:1 CH$_2$Cl$_2$/ether and filtered through a 3" plug of silica. The colorless filtrate was concentrated to approximately 20 mL under reduced pressure and a large excess of hexane added, resulting in the formation of a large quantity of crystalline 3. The mixture was further concentrated under reduced pressure to remove CH$_2$Cl$_2$ and ether, and additional hexane added. Following storage overnight at -20° C., the mother liquor was removed via cannula and discarded, the crystals washed with hexane (25 mL), and dried thoroughly under vacuum to afford crystalline (2R,4S,5R)-2,5-Diphenyl-3,4-dimethyloxazaphospholidene borane (3) in nearly quantitative yield.

2: $^1$H NMR (CDCl$_3$): δ7.5–7.2 (m, 10H, Ph); δ5.5 (d, J$_{HH}$=6.9 Hz, 1H, C(H)Ph); δ3.3–3.2 (dq, J$_{HH}$=2.3, 6.7 Hz, 1H, C(H)Me); δ2.6 (d, J$_{PH}$=13.8 Hz, 3H, N(CH3)); δ0.70 (d, J$_{HH}$=6.5 Hz, 3H, C(H)(CH$_3$)). $^{31}$P NMR (CDCl$_3$): δ59.4 (s).

3: $^1$H NMR (CDCl$_3$): δ7.9–7.3 (m, 10H, Ph); δ5.6 (dd, J$_{HH}$=3.0, 6.0 Hz, 1H, C(H)Ph); δ3.7–3.6 (dm, 1H, C(H)Me); δ2.7 (d, J$_{PH}$=11.0 Hz, 3H, N(CH$_3$)); δ0.82 (d, J$_{HH}$=6.5 Hz, 3H, C(H)(CH$_3$)); δ1.5–0.5 (br, 3H, BH$_3$). $^{31}$P NMR (CDCl$_3$): δ133.6 (br m, J$_{PB}$=83.4 Hz).

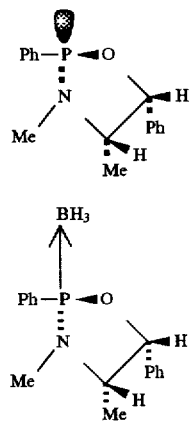

Example 4
Preparation of (Sp)-[Ph(o-Anisyl)P-N(Me)-C(H)Me-C(H)(OH)Ph]·BH$_3$ (4).

(2R,4S,5R)-2,5-Diphenyl-3,4-dimethyloxazaphospholidene borane (3, 15.8 g, 55.3 mmol) was placed in a flame-dried 200 mL Schlenk flask equipped with an addition funnel. The apparatus was then evacuated and the addition funnel flame-dried, allowed to cool under vacuum and then the system backfilled with nitrogen. In a separate flame-dried 100 mL Schlenk flask equipped with an addition funnel, distilled ortho-bromoanisole (1.3 equiv., 71.9 mmol, 13.5 g, 9.0 mL) was dissolved in 20 mL freshly-distilled THF and the resulting solution cooled to -50° C. The addition funnel was then charged with Bu"Li (1.4 equiv. vs. 3, 77.4 mmol, 48.4 mL of a 1.6 M solution in hexane) via syringe and the solution added dropwise to the ortho-bromoanisole solution over approximately 30 min. while maintaining the temperature at -50° C. During this time, a pale yellow color developed as ortho-anisyllithium was generated. When the addition of Bu"Li was complete, the mixture was stirred for 15 min. at low temperature, allowed to warm to room temperature, and stirred for an additional 45 min. During this time, freshly-distilled THF (approximately 60 mL) was added to the flask containing 3 and the solution cooled to -78° C. The pale yellow ortho-anisyllithium solution was then transferred to the addition funnel via cannula and added dropwise to the solution containing 3 over approximately 45 min. during which time, a bright yellow color developed. When the addition of o-AnLi was complete, the mixture was stirred overnight and allowed to warm slowly to room temperature. The resulting pale yellow solution was then quenched with 50 mL H$_2$O causing separation of a pale yellow organic phase. The organic layer was removed via cannula and the aqueous layer extracted 3×25 mL with 1:1 CH$_2$Cl$_2$/ether. The initial organic layer and extracts were combined and dried over Na$_2$SO$_4$. The mixture was then filtered through a 4" plug of silica and the silica washed thoroughly with ether. The colorless filtrate was concentrated via rotary evaporation, giving a pale yellow oily residue which was taken up in 20 mL ether. Addition of 40 mL hexane caused precipitation of an oil, and immersion of the flask in liquid N$_2$ with swirling caused formation of some crystalline material. The flask was stored overnight at -20° C., causing formation of a large quantity of crystalline 4. The mother liquor was removed from the crystalline material via cannula and discarded and the crystalline mass crushed into a powder with a glass stirring rod and washed with 1:5 ether/hexane (1×10 mL). The washings were removed via cannula and discarded and the solid dried thoroughly under reduced pressure, affording pure (Sp)-[Ph(o-Anisyl)P-N(Me)-C(H)Me-C(H)-(OH)Ph]·BH$_3$ (4, 20.7 g, 52.8 mmol, 95% yield) as a microcrystalline solid.

4: $^1$H NMR (CDCl$_3$): δ7.6–6.9 (m, 14H, aryl); δ4.9 (overlapping dd, J$_{HH}$=4.6, 4.5 Hz, 1H, C(H)Ph); δ4.3 (m, J$_{HH}$=6.0 Hz, 1H, C(H)Me); δ3.6 (s, 3H, C$_6$H$_4$(OCH$_3$)); δ2.5 (d, J$_{PH}$=8.1 Hz, 3H, N(CH$_3$)); δ1.8 (br d, J$_{HH}$=3.8 Hz, 1H, OH); δ1.2 (d, J$_{HH}$=6.8 Hz, 3H, C(H)(CH$_3$)); δ1.5–0.6 (br, 3H, BH$_3$). $^{31}$P NMR (CDCl$_3$): δ59.4 (br d, J$_{BP}$=87.8 Hz).

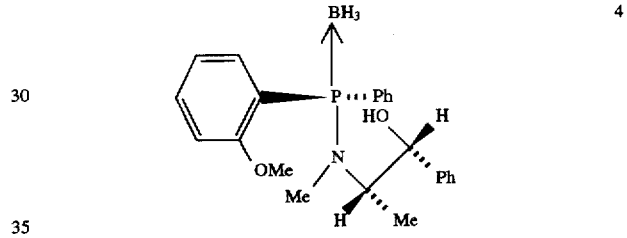

Examples 5 and 6
Preparation of (Sp)-Ph(o-Anisyl)(MeO)P·BH$_3$ (5).

(Sp)-[Ph(o-Anisyl)P-N(Me)-C(H)Me-C(H)(OH)Ph]·BH$_3$ (4, 25.6 g, 65.3 mmol) was dissolved in approximately 150 mL MeOH and the solution cooled to 0° C. Concentrated H$_2$SO$_4$ (1.1 equiv., 71.9 mmol, 4.0 mL, approximately 18M) was then added dropwise via syringe and the mixture stirred overnight and allowed to warm to room temperature. Removal of the volatiles from the mixture under reduced pressure afforded an oily residue which was diluted with 100 mL ether resulting in the formation of a white crystalline precipitate and a colorless solution. The supernatant was removed by means of a cannula tipped with filter paper and wrapped with PTFE tape and collected in a separate flask. The residual solid was washed with additional ether (3×50 mL) and the washings removed via cannula-filter and combined with the initial filtrate. Concentration of the filtrates by rotary evaporation afforded a pale yellow oil which was redissolved in 1:1 hexane/ether and chromatographed on a 1.5'×2" silica column loaded with hexane. Elution with 5–10% ether/hexane gave a large band of 5 and continued elution with 1:1 ether/hexane gave a smaller band of unreacted 4. Pure fractions were combined and concentrated via rotary evaporation to give (Sp)—Ph(o-Anisyl)(MeO)P·BH$_3$ (5,15.0 g, 57.7 mmol, 88% yield) as a viscous yellow oil. A small quantity of unreacted 4 was recovered from the second band.

The white crystalline precipitate isolated as described above was dissolved in approximately 100 mL H$_2$O and 1.0M NaOH added dropwise until the solution was strongly alkaline. The solution was then extracted with 1:1 CH$_2$Cl$_2$/ ether (4×50 mL) and the organic layers combined and dried over Na₂SO₄. The drying agent was removed by filtration and the colorless filtrates concentrated by rotary evaporator to afford (2R,3S)-1,3-dimethyl-2-phenylaziridine (6) as a viscous pale yellow oil (5.65 g, 38.4 mmol, 59% yield).

5: $^1$H NMR (CDCl₃): δ7.9–6.9 (m, 9H, aryl); δ3.7 (d, $J_{PH}$=12.1 Hz, 3H, OC$\underline{H}_3$); δ3.6 (s, 3H, C₆H₄(OC$\underline{H}_3$)); δ1.6–0.5 (br, 3H, B$\underline{H}_3$). $^{31}$P NMR (CDCl₃): δ94.8 (br q, $J_{BP}$=80.0 Hz).

6: $^1$H NMR (CDCl₃): δ7.3–7.2 (m, 5H, Ph); δ4.7 (d, $J_{HH}$=7.1 Hz, 1H, C($\underline{H}$)Ph); δ2.8–2.6 (br m, 3H, C($\underline{H}$)Me); δ2.4 (s, 3H, N(C$\underline{H}_3$)); δ0.85 (d, $J_{HH}$=11.7 Hz, 3H, C(H)C$\underline{H}_3$).

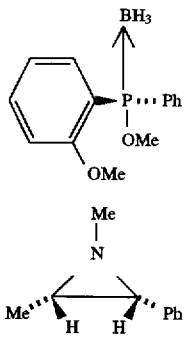

Example 7
Preparation of (Rp)-Ph(o-An)(Me)P·BH₃ (7).

(Sp)-Ph(o-Anisyl)(MeO)P·BH₃ (5, 14.4 g, 55.5 mmol) was dissolved in approximately 80 mL freshly-distilled ether and the solution cooled to −30° C. Methyllithium (1.1 equiv., 61.1 mmol, 43.6 mL of a 1.4M solution in ether) was added dropwise over approximately one hour during which time, the solution became turbid and a pale yellow color developed. The mixture was allowed to warm to 0° C. and stirring continued for one hour. The reaction was quenched with approximately 40 mL H₂O causing separation of a colorless organic phase which was removed via cannula. The aqueous layer was further extracted with ether (3×25 mL) and the extracts and initial organic layer were combined and dried over Na₂SO₄. The mixture was then filtered through a 3" plug of silica, the silica washed thoroughly with additional ether, and the colorless filtrate concentrated by rotary evaporation to approximately 20 mL. Addition of 20 mL hexane caused precipitation of an oil, and the mixture was concentrated to approximately 25 mL under reduced pressure and stored overnight at −20° C. causing crystallization of the oily precipitate. The mother liquor was removed from the crystalline material and retained in a separate flask. Spectroscopic analysis ($^1$H NMR) of the crystalline material indicated the presence of a significant quantity of unreacted 5, therefore the mother liquor and solid were recombined, dissolved in 150 mL ether and additional MeLi (15 mL) added dropwise as described above. Following work-up as described above, an oily precipitate was isolated and crystallized from hexane/ether following storage overnight at −20° C. The mother liquor was removed from the crystalline 7 via cannula and retained in a separate flask and the crystals washed with 1:4 ether/hexane. The washings were removed via cannula, combined with the initial mother liquor and the mixture concentrated to approximately 10 mL under reduced pressure affording an oily precipitate. The mixture thus obtained was stored overnight at −20° C. affording a small second crop of crystalline 7. The mother liquor was removed via cannula and discarded, the crystals washed as above and the washings discarded, and the solid dried thoroughly under reduced pressure. Combination of the two crops of crystalline material gave pure (Rp)—Ph(o-An)(Me)P·BH₃ (7, 12.2 g, 50 mmol, 90% yield).

7: $^1$H NMR (CDCl₃): δ7.9–6.8 (m, 9H, aryl); δ3.7 (s, 3H, OC$\underline{H}_3$); δ1.9 (d, $J_{PH}$=10.5 Hz, 3H, P(C$\underline{H}_3$)); δ1.5–0.5 (br, 3H, B$\underline{H}_3$). $^{31}$P NMR (CDCl₃): δ9.1 (br m, $J_{BP}$=68.8 Hz). $[\alpha_D]^{20}$=+25.2° (c=1.3, CHCl₃).

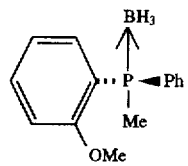

Example 8

Preparation of (Sp)-[Ph(Me)P-N(Me)-C(H)Me-C(H)(OH)Ph]·BH₃ (8).

(2R,4S,5R)-2,5-Diphenyl-3,4-dimethyloxazaphospholidene borane (3, 11.9 g, 41.9 mmol) was placed in a flame-dried 500 mL Schlenk flask equipped with an addition funnel. The system was evacuated and the addition funnel flame-dried and allowed to cool to room temperature under vacuum. The apparatus was then backfilled with nitrogen, freshly-distilled ether (250 mL) was added via cannula, and the mixture cooled to approximately −70° C. causing some precipitation of 3 therefore freshly-distilled THF (50 mL) was added in order to bring all solids into solution. The addition funnel was charged with MeLi (1.2 equiv., 50.3 mmol, 35.9 mL of a 1.4M solution in ether) via syringe and the solution added dropwise to the mixture over approximately one hour during which time, an orange color developed. When the addition of MeLi was complete, the mixture was allowed to warm to room temperature over approximately 2 hr while maintaining vigorous stirring. The orange mixture was concentrated to approximately 150 mL under reduced pressure and quenched with 40 mL H₂O, discharging the orange color and resulting in separation of a colorless organic phase. The upper organic phase was removed via cannula and the aqueous layer further extracted with ether (3×20 mL). The initial organic phase and ether extracts were combined and dried over MgSO₄. The mixture was filtered through a 3" plug of silica to remove the drying agent, the silica washed thoroughly with ether, and the colorless filtrate concentrated via rotary evaporation to approximately 50 mL. Hexane (30 mL) was added and the mixture concentrated to approximately 50 mL under reduced pressure, affording an oily precipitate. The mixture was immersed in liquid N₂, affording a white solid precipitate with swirling. The mixture was then stored for 2 hr at −20° C. to facilitate further crystallization. The mother liquor was removed from the solid mass by means of a cannula tipped with filter paper and wrapped with PTFE tape and discarded and the solid washed 1:3 ether/hexane (2×20 mL). The washings were removed via cannula-filter and discarded and the solid dried thoroughly under vacuum affording (Sp)-[Ph (Me)P-N(Me)-C(H)Me-C(H)(OH)Ph]·BH₃ (8, 13 g, nearly quantitative yield) as a white powder.

8: $^1$H NMR (CDCl₃): δ7.5–7.0 (m, 10H, Ph); δ4.9 (br d, $J_{HH}$=6.8 Hz, 1H, C($\underline{H}$Ph); δ4.0 (dq, $J_{HH}$=2.6, 6.9 Hz, 1H, C($\underline{H}$)Me); δ2.5 (d, $J_{PH}$=8.6 Hz, 3H, N(C$\underline{H}_3$)); δ2.0 (s, 1H, O$\underline{H}$); δ1.5 (d, $J_{PH}$=9.0 Hz, 3H, P(C$\underline{H}_3$)); δ1.2 (d, $J_{HH}$6.7 Hz, 3H,C(H)(C$\underline{H}_3$)); δ1.5–0.3 (br, 3H, B$\underline{H}_3$).

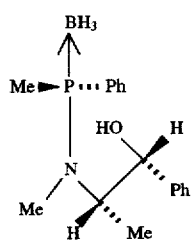

8

Examples 9 and 10
Preparation of (Sp)-Ph(Me)(MeO)P·BH₃ (9).

(Sp)-[Ph(Me)P-N(Me)-C(H)Me-C(H)(OH)Ph]·BH₃ (8, 13 g, 43 mmol) was dissolved in 100 mL MeOH and the resulting solution cooled to 0° C. Concentrated H₂SO₄ (1 equiv., 43 mmol, 2.4 mL, approximately 18M) was added dropwise via syringe and the resulting mixture stirred overnight and allowed to warm to room temperature. The volatiles were removed from the mixture under reduced pressure affording an oily residue containing a white solid. The residue was washed with ether (4×50 mL) and the washings removed from the white solid precipitate by means of a cannula tipped with filter paper and wrapped with PTFE tape and collected in a separate flask. The collected filtrate was concentrated to approximately 20 mL via rotary evaporator and filtered through a 3 " plug of silica. The silica was washed thoroughly with ether and the filtrate evaporated to dryness via rotary evaporator affording a turbid liquid which was redissolved in a minimal amount of 1:4 ether/hexane and chromatographed on a silica column (1.5"×1'- loaded with hexane). The column was washed with hexane and then eluted with 5% ether/hexane. TLC analysis indicated overlapping bands, and the fractions were combined, concentrated via rotary evaporation and rechromatographed. The column was washed thoroughly with hexane, affording a large band of 9 and continued elution with 5% ether/hexane gave a second smaller band of an unknown compound (10). Pure fractions were combined, concentrated via rotary evaporation, and dried thoroughly under reduced pressure affording (Sp)-Ph(Me)(MeO)P·BH₃ (9, 5.6 g, 40 mmol, 92% yield) as a colorless liquid and unidentified compound 10 (0.67 g) as a viscous yellowish oil.

9: ¹H NMR (CDCl₃): δ7.8–7.4 (m, 5H, P̲h̲); δ3.6 (d, J_PH=12.3 Hz, 3H, OC̲H̲₃); δ1.7 (d, J_PH=9.2 Hz, 3H, P(C H̲₃)); δ1.3–0.2 (br q of d, J_PH=15.3, J_BH=96.8 Hz, 3H, B H̲₃). ³¹P NMR (CDCl₃): δ113.5 (q, J_BP=67.1 Hz). [αD]²⁰= −91.1° (c=5.1, CHCl₃).

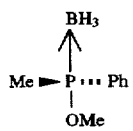

9

Examples 11 and 12
Preparation of 2,6-[(Rp)-(BH₃)(o-An)(Ph)PCH₂CH₂]₂ Pyridine (11).

(Rp)-Ph(o-An)(Me)P·BH₃ (7, 2.8 g, 11.3 mmol) was dissolved in 20 mL freshly-distilled THF and the resulting mixture cooled to −78° C. Sec-BuLi (1.1 equiv., 11.4 mmol, 8.9 mL of a 1.3M solution in cyclohexane) was added dropwise to the cooled solution over approximately 30 min., causing a color change to yellow as (Rp)-Ph(o-An)(LiCH₂) P·BH₃ was generated. After the addition was complete, the mixture was allowed to stir for 2 hr. while maintaining the temperature at approximately −78° C. In a separate flask, 2,6-bis(bromomethyl)pyridine (0.5 equiv., 5.7 mmol, 1.5 g) was dissolved in 15 mL freshly-distilled THF and the solution transferred via cannula to the addition funnel. The solution was added dropwise to the (Rp)-Ph(o-An)(LiCH₂) P·BH₃ solution over 30 min., during which time a deep red/brown color developed. The mixture was removed from the low-temperature bath and allowed to warm to room temperature over 30 min. The mixture was then quenched with 40 mL H₂O, discharging the deep red/brown color and resulting in the separation of a yellow organic phase. The upper organic phase was removed via cannula and the aqueous layer extracted further with 1:1 ether/CH₂Cl₂ (3×25 mL). The organic phase and extracts were combined, dried over Na₂SO₄, and filtered through a 3"plug of silica. The silica was washed thoroughly with 1:1 ether/CH₂Cl₂ and the pale yellow filtrate concentrated via rotary evaporation, affording a viscous yellow oil. The oil was taken up in a minimal amount of 1:1 ether/CH₂Cl₂ and chromatographed on silica gel (1.5"×1'- loaded with hexane). The product band was washed with hexane and continued elution with 10% ether/hexane gave a small band containing unreacted 7. Elution with 1:1 ether/hexane and then with 45:50:5 ether/hexane/CH₂Cl₂ gave a large band containing 11. Further elution with 30:50:20 ether/hexane/CH₂Cl₂ gave a smaller band of an unknown compound (12). Pure fractions were combined, concentrated via rotary evaporation, and then dried thoroughly under reduced pressure, affording pure 2,6-[(Rp)-(BH₃)(o-An)(Ph)PCH₂CH₂]₂pyridine (11, 2.7 g, 4.5 mmol, 70% yield) as a flocculent white solid and unknown compound 12 (0.4 g) as a flocculent solid.

11: ¹H NMR (CDCl₃): δ8.0–6.8 (m, 21H, aryl); δ3.6 (s, 6H, C₆H₄(OC̲H̲₃)); δ3.1–3.0 (overlapping dm, 4H, P(C H̲₂CH₂)Py); δ2.7–2.9 (overlapping dm, 4H, P(C H̲₂CH₂)Py), δ1.6–0.5 (br, 6H, B̲H̲₃). ¹³C NMR (CDCl₃): δ161.2 (d, J_PC=14.3 Hz, anisyl C̲(OCH₃)); δ159.7 (s, Py C̲₂); δ136.3–110.9 (Ph, An and Py); δ55.2 (s, C₆H₄(O C̲H₃)); δ31.4 (s, P(C̲H₂CH₂)Py); δ23.2 (d, J_PC=39.4 Hz, P(C H̲₂CH₂)Py). ³¹P NMR (CDCl₃): δ16.1 (br). MS (-FAB): m/z =592.5 (M⁻); 576.5 (M³¹- BH₃); 562.5 (M⁻- 2 BH₃). Anal. Calc'd for C₃₅H₄₁B₂NO₂P₂ (%): C, 71.09; H, 6.99; N, 2.37. Found: C, 70.83; H, 7.05;, N, 2.32. [α_D]²⁰=+16.70° (c=5.06, CH₂Cl₂).

12: ¹H NMR (CDCl₃): 8.0–6.8 (m, 15H, aryl); δ3.7 (s, 3H, C₆H₄(OC̲H̲₃)); δ3.2 (s, 2H, C̲H̲₂); δ3.1–2.9 (br dm, 2H, PCH₂C̲H̲₂); δ2.9–2.6 (br dm, 2H, PC̲H̲₂); δ1.5–0.5 (br, 3H, BH₃). ¹³C NMR (CDCl₃): δ161.3 (s, Py C̲₂); δ160.5 (s); δ(d, J_PC=13.4 Hz, anisyl C̲(OCH₃)); δ136.5–111.0 (Ph, An and Py ); δ55.3 (s, C₆H₄(OC̲H₃)); δ37.7 (s, C̲H₂); δ31.5 (s, P(CH₂C̲H₂)Py); δ23.5 (d, J_PC=38.5 Hz, P(C̲H₂CH₂)Py). ³¹P NMR (CDCl₃): δ16.3 (br).

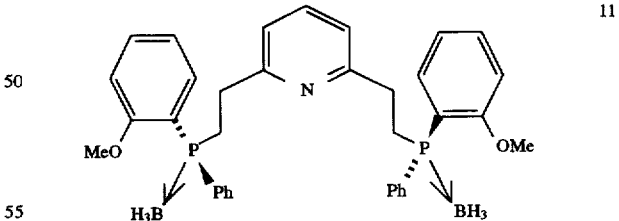

11

Example 13
Reaction of 2,6-[(Rp)-(BH₃)(o-An)(Ph)PCH₂CH₂]₂Pyridine (11) with Et₂NH.

2,6-[(Rp)-(BH₃)(o-An)(Ph)PCH₂CH₂]₂pyridine (11, 1.5 g, 2.5 mmol) was dissolved in dry, degassed Et₂NH (15 mL) and the mixture heated to reflux under nitrogen overnight. The mixture was cooled to room temperature and concentrated to approximately 5 mL under reduced pressure and diluted with 10 mL dry, degassed ether. The solution was filtered twice through neutral alumina in order to decompose Et₂NH·BH₃ and the slightly yellow filtrate was concentrated to approximately 10 mL under reduced pressure. Addition of 15 mL dry, degassed hexane, followed by concentration to approximately 10 mL caused precipitation of a viscous, colorless oil and the supernatant was removed via cannula and discarded. Spectroscopic analysis ($^{31}$P NMR) of the product indicated the reaction to be only ~90% complete, therefore the product was redissolved in Et$_2$NH and refluxed for an additional night under nitrogen. The product was worked up as above, affording 2,6-[(Rp)-(o-An)(Ph)PCH$_2$CH$_2$]$_2$pyridine (13, 1.3 g, 2.3 mmol, 92% yield) as a colorless oil.

13: $^1$H NMR (CDCl$_3$): δ7.6–6.8 (m, 21H, aryl); δ3.7 (s, 6H, C$_6$H$_4$(OCH$_3$)); δ3.0–2.8 (overlapping dm, 4H, P(CH$_2$CH$_2$)Py); δ2.4–2.7 (dm, 4H, P(CH$_2$CH$_2$)Py). $^{13}$C NMR (CDCl$_3$): δ161.3 (d, J$_{PC}$=11.5 Hz, anisyl C(OCH$_3$)); δ161.0 (d, J$_{PC}$=11.6 Hz, Py C$_2$); δ137.7–110.3 (Ph, An and Py); δ55.4 (s, C$_6$H$_4$(OCH$_3$)); δ34.6 (d, J$_{PC}$=16.3 Hz, P(CH$_2$CH$_2$)Py); δ26.1 (d, J$_{PC}$=9.3 Hz, P(CH$_2$CH$_2$)Py). $^{31}$P NMR (CDCl$_3$): δ24.9 (s).

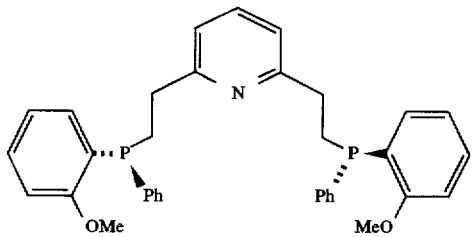

13

Example 14

Preparation of 2,6-[(Rp)-(BH$_3$)(o-An)(Ph)PCH$_2$C{O}]$_2$ Pyridine (14).

(Rp)-Ph(o-An)(Me)P·BH$_3$ (7, 2.5 g, 10.2 mmol) was dissolved in 20 mL freshly-distilled THF and the resulting mixture cooled to –78° C. Sec-BuLi (1.1 equiv., 11.3 mmol, 8.7 mL of a 1.3M solution in cyclohexane) was added dropwise to the cooled solution over approximately 30 min., causing a color change to yellow as (Rp)-Ph(o-An)(LiCH$_2$) P·BH$_3$ was generated. After the addition was complete, the mixture was allowed to stir for 2 hr. while maintaining the temperature at approximately –78° C. In a separate flask, 2,6-[(Me)(MeO)N-C{O}]$_2$pyridine (0.5 equiv., 5.1 mmol, 1.3 g) was dissolved in 15 mL freshly-distilled THF and the solution transferred via cannula to the addition funnel. The solution was added dropwise to the (Rp)-Ph(o-An)(LiCH$_2$) P·BH$_3$ solution over 30 min., during which time a deep maroon color developed. The mixture was removed from the low-temperature bath and allowed to warm to room temperature over 30 min. The mixture was then quenched with 40 mL H$_2$O containing 2 mL concentrated HCl, discharging the deep maroon color and resulting in the separation of a yellow/orange organic phase. The upper organic phase was removed via cannula and the aqueous layer extracted further with 1:1 ether/CH$_2$Cl$_2$ (3×25 mL). The organic phase and extracts were combined, dried over Na$_2$SO$_4$, and filtered through a 3" plug of silica. The silica was washed thoroughly with 1:1 ether/CH$_2$Cl$_2$ and the yellow filtrate concentrated via rotary evaporation, affording a viscous yellow oil. The oil was taken up in a minimal amount of 1:1 ether/CH$_2$Cl$_2$ and chromatographed on silica gel (1.5"×1'- loaded with hexane). The product band was washed with hexane and continued elution with 10% ether/hexane gave a small band containing unreacted 7. Elution with 1:1 ether/hexane and then with 40:50:10 ether/hexane/CH$_2$Cl$_2$ gave a large band containing 14. Several of the pure fractions produced microcrystals upon standing, and these were set aside for later use. Pure fractions were combined, concentrated via rotary evaporation, and then dried thoroughly under reduced pressure, affording 14 as a flocculent white solid. The solid was redissolved in a minimal amount of CH$_2$Cl$_2$ and ether was added until the solution became slightly turbid. Addition of several of the previously isolated microcrystals caused formation of a large crop of microcrystalline material over 1 hr and the mixture was stored overnight at –20° C. to facilitate further crystallization. The slightly colored mother liquor was removed from the crystalline material via cannula, the solid washed with ether (2×10 mL), and dried thoroughly under reduced pressure affording pure 2,6-[(Rp)-(BH$_3$)(o-An)(Ph)PCH$_2$C{O}]$_2$pyridine (14, 2.2 g, 3.6 mmol, 70% yield) as a microcrystalline solid.

14: $^1$H NMR (CDCl$_3$): δ8.1–6.7 (m, 21H, aryl); δ4.7 (overlapping dd, J$_{PH}$=12.3, J$_{HH}$=11.7 Hz, 1H, P-CH$_2$C{O}); δ4.1 (overlapping dd, J$_{PH}$=13.3, J$_{HH}$=13.6 Hz, 1H, P-CH$_2$C{O}); δ3.5 (s, 3H, C$_6$H$_4$(OCH$_3$)).δ1.6–0.4 (br, 3H,BH$_3$). $^{13}$C NMR (CDCl$_3$): δ194.3 (d, J$_{PC}$=3.5 Hz, C{O}); δ160.9 (s, anisyl C(OCH$_3$)); δ151.8 (s, Py C$_2$); δ137.9–110.8 (Ph, An and Py); δ55.0 (s, C$_6$H$_4$(OCH$_3$)); δ33.0 (d, J$_{PC}$=44.6 Hz, P(CH$_2$C{O})). $^{31}$P NMR (CDCl$_3$): δ15.3 (br). MS (-FAB): m/z=619.5 (M$^-$); 604.5 (M$^-$-BH$_3$); 590.5 (M$^-$- 2 BH$_3$). Anal. Calc'd for C$_{35}$H$_{37}$B$_2$NO$_4$P$_2$(%): C, 67.89; H, 6.02; N, 2.26. Found: C, 67.70; H, 6.07;, N, 2.32. [α$_D$]$^{20}$=–33.80° (c=5.26, CH$_2$Cl$_2$). MP: 153°–156° C. (dec).

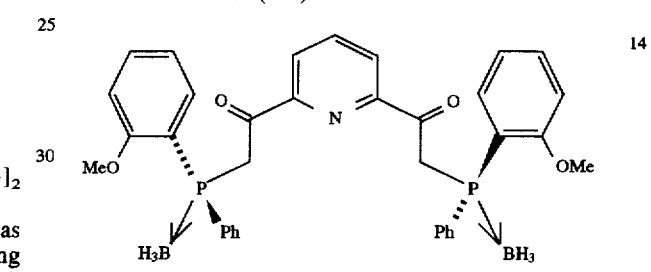

14

Example 15

Reaction of 2,6-[(Rp)-(BH$_3$)(o-An)(Ph)PCH$_2$C{O}]$_2$ Pyridine (14) with Et$_3$N in the Presence of Alumina.

2,6-[(Rp)-(BH$_3$)(o-An)(Ph)PCH$_2$C{O}]$_2$pyridine (14, 0.25 g, 0.40 mmol) was added to a flame-dried Schlenk flask containing approximately 3 g neutral alumina, the flask attached to a reflux condenser, and the system thoroughly degassed under reduced pressure. The system was then backfilled with nitrogen, attached to a bubbler with a gentle flow of nitrogen and dry, degassed Et$_3$N (20 mL) added via cannula. The heterogeneous mixture was stirred overnight at room temperature, during which time a yellow/green color developed. The solution was removed from the alumina by means of a cannula tipped with filter paper and wrapped with PTFE tape and collected in a separate flask under nitrogen. The alumina was washed with 1:1 CH$_2$Cl$_2$/ether and the washings removed via cannula-filter and combined with the initial filtrate. The yellow/green solution was evaporated to dryness under reduced pressure, affording a green/yellow viscous oil. The oil was redissolved in a minimal amount of 1:1 CH$_2$Cl$_2$/ether and the solution filtered twice through a pipette filter containing neutral alumina and each time, the filtrate was collected in a flame-dried Schlenk flask under nitrogen. The filtrate was then evaporated to dryness under reduced pressure and the resulting yellowish oily residue dried thoroughly, affording 2,6-[(Rp)-(o-An)(Ph) PCH$_2$C{O}]$_2$pyridine (15, nearly quantitative yield) as a pale yellow viscous oil.

15: $^1$H NMR (CDCl$_3$): δ8.1–6.6 (m, 21H, aryl); δ4.0 (d, J$_{PH}$=11.9 Hz, 1H, PCH$_2$C{O}Py); δ3.7 (d, J$_{HH}$=11.9 Hz, 1H, PCH$_2$C{O}Py); δ3.4 (s, 6H, C$_6$H$_4$(OCH$_3$)). $^{13}$C NMR (CDCl$_3$): δ198.0 (d, J$_{PC}$=7.6 Hz, C{O}); δ160.5 (s, anisyl C(OCH$_3$)); δ152.2 (s, Py C$_2$); δ137.6–109.9 (Ph, An and Py); δ54.8 (s, C$_6$H$_4$(OCH$_3$)); δ36.9 (d, J$_{PC}$=22.3 Hz, P( CCH₂C{O})). ³¹P NMR (CDCl₃): δ –21.5 (s).

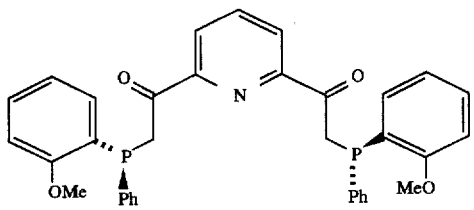

15

Example 16
Preparation of 2,6-[(Rp)-(BH₃)(o-An)(Ph)PCH₂]₂Pyridine (16).

(Rp)-Ph(o-An)(Me)P·BH₃ (7, 5.0 g, 20.5 mmol) was dissolved in 25 mL freshlydistilled THF and the resulting mixture cooled to –78° C. Sec-BuLi (1.1 equiv., 22.5 mmol, 17.3 mL of a 1.3M solution in cyclohexane) was added dropwise to the cooled solution over approximately 30 min., causing a color change to yellow as (Rp)-Ph(o-An)(LiCH₂)P·BH₃ was generated. After the addition was complete, the mixture was allowed to stir for 2 hr. while maintaining the temperature at approximately –78° C. MgBr₂ (1.1 equiv., 22.5 mmol, 4.2 g) was weighed out in an inert-atmosphere glove box and placed in a flame-dried Schlenk flask. Also in an inert-atmosphere glove box, 2,6-dibromopyridine (0.5 equiv., 10.2 mmol, 2.4 g) and (dppp)NiCl₂ (10 mol %, 2.1 mmol, 1.1 g) were weighed out and combined in a separate flame-dried three-necked, roundbottomed flask equipped with a septum, addition funnel and reflux condenser. The prepared solution of (Rp)-Ph(o-An)(LiCH₂)P·BH₃ was then transferred via cannula to the flask containing MgBr₂ and the mixture stirred 2 hr. and allowed to warm to 0° C. during which time, the yellow color of the solution lightened. The 2,6-dibromopyridine/(dppp)NiCl₂ mixture was slurried in 20 mL freshly-distilled ether and the heterogeneous mixture was cooled to 0° C. The slightly colored solution of (Rp)-Ph(o-An)(MgBrCH₂)P·BH₃ was then transferred via cannula to the addition funnel and solution added dropwise to the 2,6-dibromopyridine/(dppp)NiCl₂ mixture over 30 min. during which time, the solution became homogeneous and a deep red/brown color developed. When the addition was complete, the mixture was stirred overnight and allowed to warm to room temperature. The reaction mixture was quenched with 50 mL H₂O, causing separation of a red/black organic phase which was removed via cannula. The aqueous phase was further extracted with 1:1 CH₂Cl₂/ether (2×50 mL) and finally with CH₂Cl₂ (25 mL). The initial organic phase and extracts were combined, dried over Na₂SO₄ and filtered through a 3" plug of silica. The silica was washed thoroughly with 1:1 CH₂Cl₂/ether and the yellow/orange filtrate evaporated to dryness via rotary evaporator, affording a yellow/orange oil. Addition of a minimal amount of 1:1 CH₂Cl₂/ether caused formation of a solid precipitate and additional CH₂Cl₂ was added in order to dissolve all solids. The solution was placed on a silica gel column (1.5"×2') loaded with hexane, causing precipitation of a solid. The column was eluted with 1:1 ether/hexane, to remove a small band containing a small quantity of (Rp)-Ph(o-An)(Me)P·BH₃ (7) and 2,6-dibromopyridine. Continued elution with 1:1 ether/CH₂Cl₂ and then with CH₂Cl₂ resulted in dissolution of the solid at the top of the column and eluted a large band containing 2,6-[(Rp)-(BH₃)(o-An)(Ph)PCH₂]₂pyridine (16). Several of the fractions produced colorless microcrystals upon standing, and these were set aside for later use. The fractions containing 16 were combined and evaporated to dryness via rotary evaporation, affording an oily solid. The solid residue was taken up in a minimal amount of CH₂Cl₂ and excess ether added to the greenish solution. Addition of several of the previously isolated microcrystals to the mixture caused formation of a large crop of microcrystalline material, and additional 1:1 hexane/ether was added to facilitate further crystallization of the product. The mixture was stored at –20° C. for several hours, and then the greenish mother liquor was removed from the crystalline material via cannula and discarded. The crystals were washed with ether (3×10 mL) and dried thoroughly under reduced pressure, affording pure 2,6-[(Rp)-(BH₃)(o-An)(Ph)PCH₂]₂pyridine (16, 2.5 g, 4.5 mmol, 45% yield) as a white microcrystalline solid.

16: ¹H NMR (CDCl₃): δ7.8–6.8 (m, 21H, Aryl); δ3.8 (overlapping dm, 4H, P(C<u>H</u>₂)Py); δ3.7 (s, 6H, C₆H₄(OC<u>H</u>₃)); δ1.4–0.4 (br, 6H, B<u>H</u>₃). ¹³C NMR (CDCl₃): δ161.4 (s, anisyl <u>C</u>(OCH₃)); δ153.2 (s, Py <u>C</u>₂); δ136.1–111.4 (Ph, An and Py); δ55.4 (s, C₆H₄ (O<u>C</u>H₃)); δ34.3 (d, J<sub>PC</sub>=33.3 Hz, P(<u>C</u>H₂)Py). ³¹P NMR (CDCl₃): δ17.5 (br). MS (EI): m/z=563 (M⁺); 549 (M⁺– BH₃); 535 (M⁻– 2 BH₃). Anal. Calc'd for C₃₃H₃₇B₂NO₂P₂(%): C, 70.37; H, 6.62; N, 2.49. Found: C, 69.43; H, 6.58;, N, 2.47. |α_D|²⁰=–62.9° (c=5.13, CH₂Cl₂). MP: 183°–186° C. (dec).

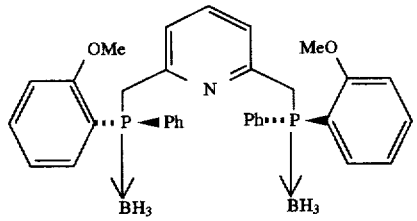

Example 17
Reaction of 2,6-[(Rp)-(BH₃)(o-An)(Ph)PCH₂]₂Pyridine (16) with Et₂NH.

2,6-[(Rp)-(BH₃)(o-An)(Ph)PCH₂]₂pyridine (16, 1.5 g, 2.7 mmol) was placed in a flame-dried Schlenk flask, the flask attached to a reflux condenser and the system thoroughly degassed under reduced pressure. The system was backfilled with nitrogen attached to a bubbler, and dry, degassed Et₂NH (15 mL) added, giving a suspension. The mixture was heated to reflux overnight under a gentle flow of nitrogen during which time, all solid dissolved and a yellow/green color developed. The mixture was allowed to cool to room temperature, concentrated to approximately 5 mL under reduced pressure and 5 mL dry, degassed CH₂Cl₂ added. The resulting solution was filtered via cannula through an alumina pipette filter and the pale yellow/green filtrate collected in a flame-dried Schlenk flask under nitrogen. The filtrate was evaporated to dryness under reduced pressure, affording a viscous greenish oil. Spectroscopic analysis (³¹P NMR) of the residue indicated the reaction to be incomplete, therefore the oil was redissolved in dry, degassed Et₂NH and the mixture refluxed for an additional night as above. Following work-up procedures as outlined above, a viscous greenish oil was obtained. The oily residue was taken up in a minimal amount of freshly-distilled ether and dry, degassed hexane added until the solution became slightly turbid. The mixture was magnetically stirred at room temperature, resulting in the precipitation of a white powder. The mixture was concentrated under reduced pressure and additional hexane added to facilitate the precipitation of additional product. The mixture was stirred at room temperature until no additional precipitate was observed and the supernatant was removed via cannula and discarded. The white powder was washed with 1:1 ether/hexane (3×5 mL), the washings discarded, and the solid dried thoroughly under reduced pressure affording pure 2,6-[(Rp)-(BH₃)(o-An)(Ph) PCH₂]₂pyridine (17, 1.2 g, 2.2 mmol, 82% yield).

17: ¹H NMR (CDCl₃): δ7.6–6.7 (m, 21H, Aryl); δ3.7 (d, J<sub>HH</sub>=14.0 Hz, 2H, P(C<u>H</u>₂)Py); δ3.7 (s, 6H, C₆H₄(OC<u>H</u>₃)); δ3.5 (d, J<sub>HH</sub>=11.4 Hz, 2H, P(C<u>H</u>₂)Py). ¹³CNMR (CDCl₃):

δ161.0 (d, $J_{PC}$=9.3 Hz, anisyl $\underline{C}$(OCH$_3$)); δ157.9 (d, $J_{PC}$= 13.9 Hz, Py $\underline{C}_2$); δ137.8–110.2 (Ph, An and Py); δ55.4 (s, C$_6$H$_4$(O$\underline{C}$H$_3$)); δ36.9 (d, $J_{PC}$=16.2 Hz, P($\underline{C}$H$_2$)Py). $^{31}$P NMR (CDCl$_3$): δ–19.8 (s). $[\alpha_D]^{20}$=+12.8° (c=5.20, CH$_2$Cl$_2$).

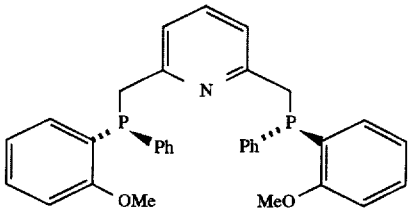

Example 18

Preparation of 1,3-[(Rp)-(BH$_3$)(o-An)(Ph)PCH$_2$CH$_2$]$_2$ Benzene (18).

(Rp)-Ph(o-An)(Me)P·BH$_3$ (7, 2.2 g, 9.0 mmol) was dissolved in 20 mL freshlydistilled THF and the resulting mixture cooled to –78° C. Sec-BuLi (1.1 equiv., 9.9 mmol, 7.6 mL of a 1.3M solution in cyclohexane) was added dropwise to the cooled solution over approximately 30 min., causing a color change to yellow as (Rp)-Ph(o-An)(LiCH$_2$)P·BH$_3$ was generated. After the addition was complete, the mixture was allowed to stir for 2 hr. while maintaining the temperature at approximately –78° C. In a separate flask, α,α'-dibromo-m-xylene (0.5 equiv., 4.5 mmol, 1.2 g) was dissolved in 15 mL freshly-distilled THF and the solution transferred via cannula to the addition funnel. The solution was added dropwise to the (Rp)-Ph(o-An)(LiCH$_2$)P·BH$_3$ solution over 45 min., during which time the yellow color of the lithium reagent faded. When the addition was complete, the mixture was stirred for 1 hr. and allowed to warm slowly to 0° C. The reaction was quenched with 40 mL H$_2$O, resulting in the separation of a pale yellow organic phase which was removed via cannula. The aqueous layer was further extracted with 1:1 CH$_2$Cl$_2$/ether (3×50 mL) and the extracts removed via cannula. The initial organic phase and extracts were combined, dried over Na$_2$SO$_4$, and the mixture filtered through a 3" plug of silica. The silica was washed thoroughly with CH$_2$Cl$_2$ and the pale yellow filtrate evaporated to dryness via rotary evaporator, affording a pale yellow viscous oil. The oil was redissolved in a minimal amount of ether and chromatographed on a silica gel column (1"×1') loaded with hexane. The product band was washed with hexane and then with 1:3 ether/hexane which eluted a band containing 7. Continued elution with 1:1 ether/hexane and then with 45:50:5 hexane/ether/CH$_2$Cl$_2$ gave a large band containing impure 18. The fractions containing 18 were combined and evaporated via rotary evaporator to give a flocculent solid which was redissolved in a minimal amount of ether and rechromatographed. The product band was washed thoroughly with 10% ether/hexane and the product then eluted with 45:50:5 hexane/ether/CH$_2$Cl$_2$. The fractions were combined and evaporated to dryness via rotary evaporator to give a colorless oil. Thorough drying of the oily residue under reduced pressure afforded pure 1,3-[(Rp)-(BH$_3$)(o-An)(Ph)PCH$_2$CH$_2$]$_2$benzene (18, 2.2 g, 3.7 mmol, 83% yield) as a flocculent solid.

18: $^1$H NMR (CDCl$_3$): δ8.1–6.8 (m, 22H, Aryl); δ3.7 (s, 6H, C$_6$H$_4$(O$\underline{C}$H$_3$)); δ3.1–2.8 (br dm, 4H, P(CH$_2$C$\underline{H}_2$)(C$_6$H$_4$)); δ2.5–2.7 (br dm, 4H, P(C$\underline{H}_2$CH$_2$)(C$_6$H$_4$)); δ1.6–0.5 (br, 6H, B$\underline{H}_3$). $^{13}$C NMR (CDCl$_3$): δ161.3 (s, anisyl $\underline{C}$(OCH$_3$)); δ141.8–111.1 (Aryl); δ55.3 (s, C$_6$H$_4$(O$\underline{C}$H$_3$)); δ29.3 (s, P(CH$_2$$\underline{C}$H$_2$)(C$_6$H$_4$)); δ26.0 (d, $J_{PC}$=38.4 Hz, P($\underline{C}$H$_2$CH$_2$)(C$_6$H$_4$)). $^{31}$P NMR (CDCl$_3$): δ16.0 (br). MS (EI): m/z=590 (M$^{+}$); 576 (M$^{+-BH}_3$); 562 (M$^{+-}$ 2 BH$_3$).

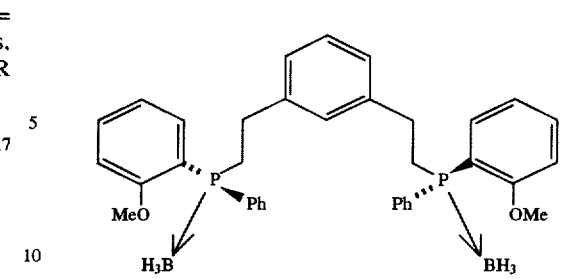

Example 19

Reaction of 1,3-[(Rp)-(BH$_3$)(o-An)(Ph)PCH$_2$CH$_2$]$_2$ Benzene (18) with Et$_2$NH.

1,3-[(Rp)-(BH$_3$)(o-An)(Ph)PCH$_2$CH$_2$]2Benzene (18, 1.0 g, 1.7 mmol) was placed in a flame-dried Schlenk flask, the flask attached to a reflux condenser, and the system thoroughly degassed under reduced pressure. The system was then backfilled with nitrogen, attached to a bubbler, and dry, degassed Et$_2$NH (10 mL) added via cannula. The mixture was heated to reflux overnight while maintaining a gentle flow of nitrogen. The mixture was allowed to cool to room temperature, concentrated to approximately 3 mL under reduced pressure, and diluted with 10 mL dry, degassed ether. The solution was filtered through an alumina pipette filter and the colorless filtrate collected in a flame-dried Schlenk flask under nitrogen. The filtrate was evaporated to dryness under reduced pressure and thoroughly dried, affording pure 1,3-[(Rp)-(o-An)(Ph)PCH$_2$CH$_2$]2benzene (19, nearly quantitative yield) as a colorless oil.

19: $^1$H NMR (CDCl$_3$): δ7.6–6.8 (m, 22H, Aryl); δ3.8 (s, 6H, C$_6$H$_4$(OC$\underline{H}_3$)); δ2.7–2.9 (overlapping dm, 4H, P(CH$_2$C$\underline{H}_2$)C$_6$H$_4$); δ2.3–2.6 (ddt, $J_{HH}$=12.2, 5.4; $J_{PH}$=58.0 Hz, 4H, P(C$\underline{H}_2$CH$_2$)C$_6$H$_4$). $^{13}$C NMR (CDCl$_3$): δ161.0 (d, $J_{PC}$=12.9 Hz); δ142.9 (d, $J_{PC}$=12.2 Hz, anisyl $\underline{C}$(OCH$_3$)); δ137.5–110.2 (aryl); δ55.3 (s, C$_6$H$_4$(O$\underline{C}$H$_3$)); 32.1 (d, $J_{PC}$= 19.4 Hz, P($\underline{C}$H$_2$CH$_2$)C$_6$H$_4$); δ28.1 (d, $J_{PC}$=11.1 Hz, P(CH$_2$$\underline{C}$H$_2$)Py). $^{31}$P NMR (CDCl$_3$): δ–24.9 (s).

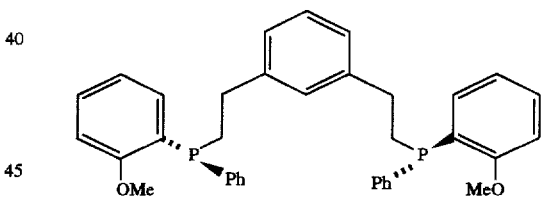

Example 20

Preparation of 2,6-[(Sp)-(BH$_3$)(OMe)(Ph)PCH$_2$CH$_2$]$_2$ Pyridine (20).

(Sp)-Ph(Me)(MeO)P·BH$_3$ (9, 2.0 g, 14.2 mmol) was placed in a flame-dried Schlenk flask, the flask attached to an addition funnel, and the system thoroughly degassed under reduced pressure. Freshly-distilled THF (20 mL) was then added via syringe and the solution cooled to –78° C. Sec-BuLi (1.1 equiv., 15.6 mmol, 12 mL of a 1.3M solution in cyclohexane) was added to the solution dropwise over 30 min. during which time, a bright yellow color developed and a precipitate formed. When the addition was complete, the reaction mixture (containing (Sp)-Ph(LiCH$_2$)(MeO)P·BH$_3$) was allowed to stir for an additional 30 min. while the temperature was maintained at –78° C. In a separate flask, 2,6-bis(bromomethyl)pyridine (0.5 equiv., 7.1 mmol, 1.9 g) was dissolved in 15 mL freshly-distilled THF and the solution transferred to the addition funnel via cannula. The solution was added to the yellow reaction mixture over 30 min. while the temperature was maintained at –70° C. During this time, the solution became deep red and when the addition was complete, the mixture was stirred for an additional hour and allowed to warm to approximately -10° C. The reaction was quenched with 20 mL H₂O, discharging the deep red color and resulting in the separation of a yellow organic phase. The upper organic layer was removed via cannula and the aqueous phase extracted further with 1:1 ether/CH₂Cl₂ (2×20 mL). The initial organic phase and extracts were combined, dried over Na₂SO₄, and the mixture filtered through a 3" plug of silica. The silica was washed thoroughly with 1:1 ether/CH₂Cl₂ and the pale yellow filtrate evaporated to dryness via rotary evaporator, affording a yellow oily residue. The residue was taken up in a minimal amount of ether and chromatographed on silica gel (2"×1.5'-loaded with hexane). The product band was washed with hexane, followed by 5–10% ether/hexane. Continued elution with 1:1 ether/hexane and then with 45:50:5 hexane/ether/CH₂Cl₂ gave a large band containing 2,6-[(Sp)-(BH₃)(OMe)(Ph)PCH₂CH₂]₂pyridine (20). The fractions were combined and evaporated to dryness, affording a pale yellow viscous oil. The oil was thoroughly dried under reduced pressure, affording pure 2,6-[(Sp)-(BH₃)(OMe)(Ph)PCH₂CH₂]₂pyridine (20, 2.1 g, 4.8 mmol, 67% yield) as a viscous oil.

20: $^1$H NMR (CDCl₃): δ7.8–7.4 (m, 10H, Ph); δ7.4 (t, $J_{HH}$=7.7 Hz, 1H, pyridine p-C-$\underline{H}$); δ6.9 (d, $J_{HH}$=7.7 Hz, 2H, pyridine m-C-$\underline{H}$); δ3.6 (d, $J_{PH}$=11.9 Hz, 6H, P(OC$\underline{H}_3$)); δ2.8–3.0 (br dm, 4H, P(CH₂C$\underline{H}_2$)Py); δ2.3–2.5 (br dm, 4H, P(C$\underline{H}_2$CH₂)Py), δ1.4–0.3 (br, 6H, B$\underline{H}_3$). $^{31}$P NMR (CDCl₃): δ117.5 (br m, $J_{PB}$=50.5 Hz). MS (+FAB): m/z =438 (M - H$^+$); 424 (M - (H$^+$+BH₃)).

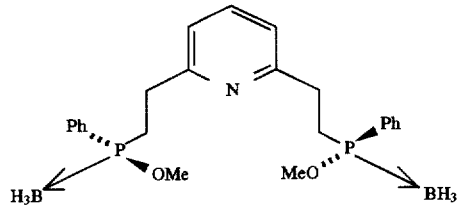

Example 21
Reaction of 2,6-[(Sp)-(BH₃)(OMe)(Ph)PCH₂CH₂]₂Pyridine (20) with MeLi.

2,6-[(Sp)-(BH₃)(OMe)(Ph)PCH₂CH₂]₂pyridine (20, 1.4 g, 3.1 mmol) was dissolved in 20 mL freshly-distilled THF and the solution cooled to -78° C. Methyllithium (4.2 equiv., 13.0 mmol, 9.3 mL of a 1.4 mL solution in ether) was added dropwise over 30 min. during which time, a deep red color developed. Upon completion of the addition, stirring was maintained for 45 min. and the solution allowed to warm to approximately -10° C. The reaction was quenched with 25 mL H₂O, discharging the red color and resulting in the separation of a yellow organic phase. The upper organic phase was removed via cannula and the aqueous layer further extracted with 1:1 ether/CH₂Cl₂ (2×20 mL). The initial organic phase and extracts were combined, dried over Na₂SO₄, and the mixture filtered through a 3" plug of silica. The silica was washed thoroughly with additional 1:1 ether/CH₂Cl₂ and the pale yellow filtrate concentrated via rotary evaporator, affording a yellow oil. The oily residue was taken up in a minimal amount of 1:1 ether/CH₂Cl₂ and chromatographed on silica gel (1"×1'-loaded with hexane). The product band was washed with hexane and then with 10% ether/hexane, eluting a small band containing Ph(Me)(H)P·BH₃ (by $^1$H NMR) which was discarded. Continued elution with 45:50:5 hexane/ether/CH₂Cl₂ gave a large band containing 2,6-[(Rp)-(BH₃)(Me)(Ph)PCH₂CH₂]₂pyridine (21). The fractions were combined, evaporated to dryness via rotary evaporator and thoroughly dried under reduced pressure, affording 21 as a viscous, turbid oil. Dissolution of the oily residue in a minimal amount of 1:1 ether/CH₂Cl₂, followed by addition of excess hexane resulted in the precipitation of an oil. Concentration of the solution under reduced pressure, followed by immersion of the flask in liquid N₂ with swirling caused solidification of the oil and a white precipitate was obtained. The solution was concentrated further under reduced pressure and additional hexane added to facilitate additional precipitation of the product and the mother liquor removed via cannula and discarded. The solid was washed with hexane (2×10 mL) and dried thoroughly under reduced pressure, affording pure 2,6-[(Rp)-(BH₃)(Me)(Ph)PCH₂CH₂]₂pyridine (21, 0.89 g, 2.2 mmol, 70% yield) as a free-flowing white powder.

21: $^1$H NMR (CDCl₃): δ7.7–7.3 (m, 11H, Ph and pyridine p-C-$\underline{H}$); δ6.9 (d, $J_{HH}$=7.7 Hz, 2H, pyridine m-C-$\underline{H}$); δ3.0–2.6 (overlapping dm, 4H, P(CHC$\underline{H}_2$)Py); δ2.4–2.2 (overlapping dm, 4H, P(CH₂C$\underline{H}_2$)Py), δ1.6 (d, $J_{PH}$=10.2 Hz, 6H, P(C$_{H3}$); δ1.4–0.3 (br, 6H, B$\underline{H}_3$). $^{13}$C NMR (CDCl₃): δ159.3 (d, $J_{PC}$=13.2 Hz, Py $\underline{C}_2$); δ136.9–120.4 (Ph and Py ); δ31.1 (s, P(CH₂$\underline{C}$H₂)Py); δ26.5 (d, $J_{PC}$=36.2 Hz, P(C$\underline{H}_2$CH₂)Py); δ10.9 (d, JP$_C$=80.2 Hz, P(C$\underline{H}_3$)). $^{31}$P NMR (CDCl₃): δ10.1 (br m, $J_{PB}$=71.5 Hz). MS(+FAB): m/z =406 (M - H$^+$); 392 (M - (H$^+$+BH₃)).

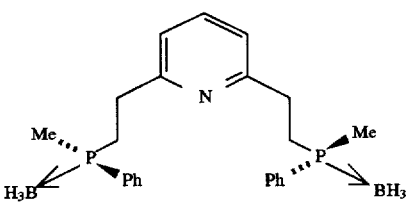

Example 22
2,6-Pyridinedicarboxylic acid dichloride 2,6-pyridinedicarboxylic acid (111 g, 0.665 mol) was suspended in thionyl chloride (350 ml, 4.8 mol) and heated to be refluxed overnight until it became a clear solution. The excess of thionyl chloride was removed under reduced pressure. The resulting solid was ground to powder and dried under vacuum. The reaction was quantitative. $^1$H-NMR (CDCl₃): dH=8.36 (d, $^3$J(HH)=7.8 Hz, 2 H, H$_{3,5}$), 8.17 (t, $^3$J(HH)=7.8 Hz, 1 H, H₄). $^{13}$C-NMR (CDCl₃): dC=169.32 (C=O), 149.24 (C$_{2,6}$), 139.41 (C₄) and 128.97 (C$_{3,5}$).

Example 23
2,6-Diacetylpyridine

MeLi in ether (185 ml, 259 mmol) was added over one hour into the cooled (-78° C.) suspension of CuI (I) (47.5 g, 249 mmol) in ether (100 ml) and THF (300 ml). The resulting yellow suspension was slowly warmed up to -20° C. over about one hour, then cooled to -78° C. again. 2,6-pyridinedicarboxylic acid dichloride (Example 22, 19.1 g, 93.6 mmol) in THF (100 ml) was added over 30 minutes. The resulting orange-yellow suspension was stirred at temperature lower than -30° C. for 2.5 hours and then hydrolyzed with saturated NH₄Cl—H₂O. After warmed up to room temperature, the color of the aqueous phase changed from light orange to blue. The mixture was filtered through Celite, and washed consecutively with ether and CH₂Cl₂. The organic phase was separated off. The aqueous phase was extracted consecutively with ether (2×80 ml) and CH₂Cl₂ (80 ml). The combined organic solutions were dried over Na₂SO₄, and then filtered. After removal of solvents, the residue was subjected to chromatography on a silica gel column, eluted with hexane/AcOEt (16:1), giving white or pale yellow solid. Yield: 14.2 g (93%). $^1$H-NMR (CDCl₃): dH=8.18 (d, $^3$J(HH)=7.7 Hz, 2 H, H$_{3,5}$), 7.96 (dd, $^3$J(HH)= 8.2 and 7.3 Hz, 1 H, H₄), 2.76 (s, 6 H, CH₃). $^{13}$C-NMR (CDCl₃): dC=199.17 (C=O), 152.46 (C$_{2,6}$), 137.74 (C₄), 124.51 (C$_{3,5}$), 25.32 (CH₃).

Example 24

(S,S)-(−)-α,α'-Dimethyl-2,6-pyridinedimethanol (−)-DIP-Cl (about 70% in hexane, about 22 mmol) was evaporated under reduced pressure to remove hexane. The resulting oil was dissolved in THF (15 ml) and added over 5 minutes into the solution of 2,6-diacetylpyridine (Example 23, 1.0 g, 6.13 mmol) in THF (20 ml) which had been cooled to −18° C. with ice-salt bath. The resulting orange solution was stirred at −18° C. to room temperature for 24 hours. Ether (60 ml) was added. The solution was cooled to 0° C. and then (HOCH$_2$CH$_2$)$_2$NH (5 ml, 52 mmol) was added. The resulting suspension was stirred at 0° C. to room temperature for 6 hours and filtered through Celite. The filtrate was evaporated to dryness. The residue was taken into ether/hexane, and filtered again. This operation was repeated a few times until there was little solid left when the residue was treated with ether/hexane. The final residue was subjected to chromatography on silica gel column, eluted consecutively with hexane/AcOEt (8:1) hexane/AcOEt (1:4). The crude product obtained was subjected to chromatography on a silica gel column again, and eluted consecutively with hexane/AcOEt (8:1), hexane/AcOEt/Et$_3$N (800:600:14), hexane/AcOEt (1:3). From hexane/AcOEt/Et$_3$N (800:600:14) eluant, (S)-(−)-6-acetyl-a-methyl-2-pyridinemethanol was obtained. From hexane/AcOEt (1:3) eluant monitored by chiral GC column (fused silica capillary column, SUPLECO β-DEX# 120, 30 m×0.25 mm, 150° C.), (S,S)-(−)-α,α'-dimethyl-2,6-pyridinedimethanol pyridinedimethanol was obtained. Yield: 0.41 g (40%). EE: 98%, containing 0.5% meso-isomer. $^1$H-NMR (CDCl$_3$): dH=7.68 (t, $^3$J(HH)=7.7 Hz, 1 H, H-gpy), 7.20 (d, $^3$j(HH)= 7.7 Hz, 2 H, H-bpy), 4.88 (q, $^3$J(HH)=6.6 Hz, 2 H, CH), 3.94 (s, broad, 2 H, OH), 1.49 (d, J(HH)=6.6 Hz, 6 H, CH$_3$). $^{13}$C-NMR (CDCl$_3$): dC=162.06 (C$_{2,6}$), 137.64 (C$_4$), 118.26 (C$_{3,5}$), 69.18 (CHOH), 24.07 (CH$_3$).

Example 25

Ditosylate of (S,S)-(−)-α,α'-dimethyl-2,6-pyridinedimethanol (S,S)-(−)-α,α'-dimethyl-2,6-pyridinedimethanol (Example 24, 1.0 g, 5.98 mmol) in toluene (30 ml) was added over 5 min into the cooled (lower than 0° C., with ice-salt bath) suspension of NaH (0.71 g, 29.6 mmol) in toluene (20 ml). The resulting pale suspension was stirred at same temperature for another 40 minutes p-Toluenesulfonyl chloride (4.56 g, 23.9 mmol) in toluene (30 ml) was added over 10 min. The resulting suspension was stirred at 0° C. to room temperature for 42 hour and then poured into ice—H$_2$O with fast stirring. After separation of the organic phase, the aqueous phase was extracted with CH$_2$Cl$_2$ (2×50 ml). The combined organic solutions were dried over MgSO$_4$/Na$_2$SO$_4$, and filtered. After removal of solvents, the residue was subjected to chromatography on a silica gel column, eluted consecutively with hexane/AcOEt (8:1) to remove the excess of p-Toluenesulfonyl chloride, hexane/AcOEt (8:4) to get the ditosylate, hexane/AcOEt (8:6) to obtain the monotosylate. For ditosylate of (S,S)-(−)-α,α'-dimethyl-2,6-pyridinedimethanol: EE: 96% determined by BPLC analysis using a chiralcel® OD column with hexane/isopropanol (90:10). $^1$H-NMR (CDCl$_3$): dH=7.70 (d, br, $^3$J(HH)=8.3 Hz, 4 H, H$_{ortho}$), 7.54 (t, $^3$J(HH)=7.8 Hz, 1 H, H$_4$), 7.24 (d, br, $^3$J(HH)=8.3 Hz, 4 H, H$_{meta}$), 7.20 (d, $^3$J(HH)=7.8 Hz, 2 H, H$_{3,5}$), 5.51 (q, $^3$J(HH)=6.6 Hz, 2 H, CH), 2.39 (s, 6 H, CH$_3$-pTs), 1.51 (d, $^3$J(HH)=6.6 Hz, 6 H, CH$_3$). $^{13}$C-NMR (CDCl$_3$): dC=157.69 (C$_{2,6}$), 144.50 (C$_{para}$), 137.41 (C$_4$), 133.66 (C$_{ipso}$), 129.50 ($_{meta}$), 127.62 (C$_{ortho}$), 119.52 (C$_{3,5}$), 80.26 (CHOTs), 21.39 (CH$_3$), 21.36 (CH$_3$).

Example 26

(R,R)-2,6-Bis(1-diphenylphosphinoethyl)pyridine

Ph$_2$PH (2.16 ml, 12.1 mmol) was dissolved in ether (50 ml) and cooled to −78° C. $^n$BuLi in hexane (7.6 ml, 12.2 mmol) was added with syringe over 15 min. The resulting yellow suspension was warmed slowly up to room temperature and stirred at same the temperature for another one hour, leading to an orange solution which was cooled to −78° C. again. (S,S)-2,6-bis((α-p-toluenesulfonyloxy)ethyl)pyridine (Example 25, 2.8 g, 5.89 mmol) in THF (50 ml) was added over 50 minutes. On adding the ditosylate solution, the yellow Ph$_2$PLi suspension changed to orange-red solution. The resulting orange-red suspension was warmed slowly up to room temperature and stirred at the same temperature overnight, resulting in a pale suspension. Degassed H$_2$O (50 ml) was added. The organic solution was separated off, the aqueous layer was extracted with CH$_2$Cl$_2$ (2×30 ml). The combined organic solutions were dried overnight over Na$_2$SO$_4$, and filtered. After removal of solvents, the residue was taken into hexane (100 ml) and filtered. The colorless hexane filtrate was concentrated under reduced pressure to about 20 ml and then cooled to −78° C. The white solid formed was filtered off and washed with hexane (20 ml) at −78° C. After dried at room temperature under vacuum, 2.9 g (98%) white solid was obtained. $^{31}$P-NMR (CDCl$_3$): dP=1.6 ppm. $^1$H-NMR (CDCl$_3$): dH=7.70–7.55 (m, 4 H, aromatic), 7.50–7.35 (m, 6 H, aromatic), 7.31 (t, $^3$J(HH)=7.7 Hz, 1 H, H$_4$), 7.25–7.05 (m, 10 H, aromatic), 6.95 (d, $^3$J(HH)=7.7 Hz, 2 H, H$_{3,5}$), 3.76 (psedo quintet, $^2$J(PH)=6.9 Hz, $^3$J(HH)=7.1 Hz, 2 H, CHPPh$_2$), 1.37 (dd, $^3$J(PH)=14.7 Hz, $^3$J(HH)=7.1 Hz, 6 H, CH$_3$). $^{13}$C-NMR (CDCl$_3$): dC=162.37 (d, $^2$J(PH)=8.8 Hz, C$_{2,6}$), 137.37 (d, $^1$J(PH)=14.6 Hz, C$_{ipso}$), 137.16 (d, $^1$J(PH)=15.8 Hz, C$_{ipso}$), 136.19 (C$_{3,5}$), 134.01 (d, $^2$J(PH)=20.7 Hz, C$_{ortho}$), 133.02 (d, $^2$J(PH)=18.0 Hz, C$_{ortho}$), 128.88 (C$_{para}$), 128.21 (d, $^3$J(PH)=7.3 Hz, C$_{meta}$), 127.87 (C$_{para}$), 127.69 (d, $^3$J(PH)=6.2 Hz, C$_{meta}$), 119.84 (d, $^3$J(PH)=Hz, C$_{3,5}$), 41.39 (d, $^1$J(PH)=11.4 Hz, CH), 18.89 (d, $^2$J(PH)=19.7 Hz, CH$_3$).

Example 27

2,6-Bis(2',2'-dimethylpropionyl)pyridine $^t$BuOH (10.0 ml, 105 mmol) was dissolved in THF (50 ml) and cooled to 0° C. $^n$BuLi, 1.6M in hexane, (66 ml, 106 mmol) was added over 30 minutes. The resulting light pale yellow solution was stirred at 0° C. for one hour. This Bu$^t$OLi solution was then added over 30 minutes into the suspension of CuI (I) (20.0 g, 105 mmol) in THF (100 ml) which was cooled to 0° C. The resulting orange-brown suspension was stirred at room temperature for 45 minutes and then cooled to −78° C. $^t$BuLi, 1.7M in pentane, (62 ml, 105 mmol) was added over 50 minutes and stirred at same temperature for another one hour, giving orange-gray suspension. 2,6-pyridinedicarboxylic acid dichloride (8.2 g, 40.2 mmol) in THF (80 ml) was added over 40 minutes, leading to a dark red-brown solution. The stirring was continued for another one hour at −78° C., then MeOH (40 ml) was added over 5 minutes. The mixture was stirred for about 20 minutes and then warmed up to room temperature, whereupon it became black. Saturated NH$_4$Cl—H$_2$O (400 ml) was added. The organic solution was separated off The aqueous layer was extracted with ether (4×50 ml). The combined organic solutions were dried overnight over Na$_2$SO$_4$. After filtered, the solvents were removed under reduced pressure. The crude product was subjected to chromatography on silica gel column, eluted with hexane/AcOEt (16:1). Yield: 8.1 g (82%). $^1$H-NMR (CDCl$_3$): dH=8.05–7.85(m, 3 H, aromatic) and 1.47 (s, 18 H, CH$_3$). $^{13}$C-NMR (CDCl$_3$): dC=205.46 (C=O), 153.44 (C$_{2,6}$), 137.69 (C$_4$), 125.87 (C$_{3,5}$), 43.75 (C(CH$_3$)$_3$), 27.16 (C(CH$_3$)$_3$).

Example 28

(R,R)-α,α-di-ter-butyl-2,6-pyridinedimethanol 2,6-Bis(2',2'-dimethylpripionyl)pyridine (from Example 27, 5.4 ml, 22.5 mmol) and (−)-DIP-Cl (41.2 g, 128.5 mmol)

were mixed and THF (16 ml) was added. The resulting suspension was stirred at room temperature for 9 days. It became homogeneous and light orange in color. Ether (200 ml) was added. The solution was cooled with ice—$H_2O$ bath and $(HOCH_2CH_2)_2NH$ (28 ml, 292 mmol) was added. The resulting suspension was slowly warmed up to room temperature and stirred at room temperature for about 5 hours and filtered through Celite. The filtrate was evaporated to dryness under reduced pressure. The residue was taken into ether/hexane and filtered again. These operations were repeated a few times until there was little solid left when the residue was treated with ether/hexane. The final residue was subjected to chromatography on silica gel column, eluted consecutively with hexane, hexane/AcOEt (16:1), and hexane/AcOEt (5:2). From the hexane/AcOEt (5:2) eluant, crude product was isolated a white solid which was further purified by Kugelrohr distillation at 160° C./0. mmHg. Yield: 2.4 g (42%). EE was 100% determined by GC on chiral column (fused silica capillary column, β-DEX™ 120, 30 m×0.25 mm, 178° C.). $^1$H-NMR ($CDCl_3$): dH=7.61 (t, $^3$J(HH)=7.8 Hz, 1 H, $H_4$), 7.13 (d, $^3$J(HH)=7.8 Hz, 2 H, $H_{3,5}$), 4.36 (d, $^3$J(HH)=6.6 Hz, 2 H, CH), 3.74 (d, $^3$J(HH)=6.6 Hz, 2 H, OH), 0.92 (s, 18 H, $CH_3$). $^{13}$C-NMR ($CDCl_3$): dC=158.68 ($C_{2,6}$), 135.48 ($C_4$), 121.42 ($C_{3,5}$), 80.55 (CHOH), 36.19 ($\underline{C}(CH_3)_3$), 25.85(C($\underline{C}H_3$)$_3$).

Example 29
2,6-Di(bromomethyl)pyridine 2,6-pyridinedimethanol (10.0 g, 71.9 mmol) was dissolved in 48% HBr (95 ml), concentrated $H_2SO_4$ (10 ml) was added slowly. The reaction mixture was then heated at ca. 110° C. for 19 hours. The mixture was then cooled with Ice-salt bath and neutralized with concentrated NaOH solution to basic. The white solid formed was filtered off, and washed with $H_2O$. The solid was recrystallized from hexane at −20° C. Yield: 13.1 g (69%). $^1$H-NMR ($CDCl_3$): dH=7.70 (t, $^3$J(HH)=7.7 Hz, 1 H, H-g), 7.36 (d, $^3$J(HH)=7.7 Hz, 2 H, H-b), 4.53 (s, 4 H, $CH_2$).

Example 30
2,6-Bis[2-(Rp)-boronato(o-anisylphenylphosphino)ethyl]-pyridine

In a flame-dried 100 mL Schlenk flask equipped with an addition funnel, (Rp)-Ph(o-An)(Me)P-$BH_3$ (3.3 g, 13.5 mmol) was dissolved in freshly-distilled THF (25 mL) and the resulting solution cooled to −78° C. (liquid N2/Pr$^i$OH bath). Sec-BuLi (1.1 equiv., 14.8 mmol, 11.4 mL of a 1.3M solution) was then added dropwise over approximately 30 minutes, during which time a bright yellow color developed. The resulting solution [containing ($R_P$)-Ph(o-An)($CH_2$Li)P-$BH_3$] was stirred for approximately 2 hours while maintaining the temperature at approximately −78° C. In a separate flask, 2,6-bis(bromomethyl)pyridine (from Example 29, 0.5 equiv., 1.8 g, 6.7 mmol) was dissolved in freshly-distilled THF (10 mL), and the resulting solution transferred to the addition funnel via cannula. The pyridine solution was added dropwise to the yellow reaction mixture over approximately 20 minutes while maintaining the temperature at approximately −78° C., during which time, the solution became deep red/brown. The reaction mixture was allowed to warm to room temperature over approximately 1.5 hours and then distilled water (40 mL) was added, discharging the red/brown color and causing separation of a yellow organic layer. The upper organic layer was removed via cannula and the aqueous layer extracted further with 1:1 ether/$CH_2Cl_2$ (2×20 mL). The initial organic layer and extracts were combined and dried over $MgSO_4$ overnight. The light yellow supernatant was removed by means of a cannula tipped with filter paper and wrapped with PTFE tape and collected in a separate flask. The residual drying agent was washed with additional 1:1 ether/$CH_2Cl_2$ (2×20 mL), and the washings removed via cannula-filter and combined with the initial filtrate. Removal of the volatiles from the combined filtrates under reduced pressure afforded a viscous yellow oil which was redissolved in a minimal amount of 1:1 ether/$CH_2Cl_2$ and chromatographed on $SiO_2$ (1'×2"). 10 mL fractions were collected and analyzed by TLC on $SiO_2$ plates developed with 2:1 ether/$CH_2Cl_2$. The column was initially eluted with hexane (50 mL), and then with 1:5 ether/hexane (100 mL) to elute a small quantity of unreacted (Rp)-Ph(o-An)(Me)P-$BH_3$. Continued elution with 1:1 ether/hexane (400 mL) afforded a large band containing the product of this Example, and elution with 5:4:1 ether/hexane/$CH_2Cl_2$ (200 mL) afforded a smaller band of an unidentified compound. Pure fractions were combined, concentrated by rotary evaporation, and dried thoroughly under reduced pressure to afford the product of this Example (2.7 g, 4.5 mmol, 68% yield) as a flocculent solid.

$^1$H NMR ($CDCl_3$): δ7.7–6.8 (m, 27H, Aryl); δ3.6 (s, 6H, O$\underline{C}$$H_3$); δ3.1–3.0 (br dm, 4H, $\underline{C}H_2CH_2$P); δ2.9–2.6 (br dm, 4H, $CH_2\underline{C}H_2$P); δ1.6–0.6 (br, 6H, B$\underline{H}_3$). $^{13}$C NMR ($CDCl_3$): δ161.2–110.9 (Aryl); δ55.2 (s, O$\underline{C}H_3$); δ31.4 (s, $\underline{C}H_2CH_2$P); δ23.3 (d, $J_{PC}$=39.4 Hz; $CH_2\underline{C}H_2$P). $^{31}$P NMR ($CDCl_3$): δ16.3 (br m, $J_{PB}$=39 Hz). MS (-FAB): m/z=592.5 (M$^-$); 576.4 (M$^-$- $BH_3$); 562.5 (M$^-$- 2 $BH_3$).

Example 31
2,6-Bis[1-carbonyl,2-(Rp)-boronato(o-anisylphenylphosphino)ethyl]pyridine In a flame-dried 100 mL Schlenk flask equipped with an addition funnel, (Rp)-Ph(o-An)(Me)P-$BH_3$ (2.5 g, 10.2 mmol) was dissolved in freshly-distilled THF (25 mL) and the resulting solution cooled to −78° C. (liquid N$_2$/Pr$^i$OH bath). Sec-BuLi (1.1 equiv., 11.3 mmol, 8.7 mL of a 1.3M solution) was then added dropwise over approximately 30 minutes, during which time a bright yellow color developed. The resulting solution [containing (Rp)-Ph(o-An)($CH_2$Li)P-$BH_3$] was stirred for approximately 2 hours while maintaining the temperature at approximately −78° C. In a separate flask, 2,6-pyridinedicarboxylic acid bis(N,O-dimethylhydroxylamide) (0.5 equiv., 1.3 g, 5.1 mmol) was dissolved in freshly-distilled THF (10 mL) and the resulting solution transferred to the addition funnel via cannula. The diamide solution was added dropwise to the yellow reaction mixture over approximately 20 minutes while maintaining the temperature at approximately −78° C. during which time, the solution became deep red/purple. The reaction mixture was allowed to warm to room temperature over approximately 1 hour and then distilled water (40 mL) containing concentrated HCl (2 mL, approximately 24 mmol) was added, discharging the red/purple color and causing separation of a yellow/orange organic layer. The upper organic layer was removed via cannula and the aqueous layer extracted further with 1:1 ether/$CH_2Cl_2$ (2×20 mL). The initial organic layer and extracts were combined and dried over $MgSO_4$ overnight. The yellow/orange supernatant was removed by means of a cannula tipped with filter paper and wrapped with PTFE tape and collected in a separate flask. The residual drying agent was washed with additional 1:1 ether/$CH_2Cl_2$ (2×20 mL), and the washings removed via cannula-filter and combined with the initial filtrate. Removal of the volatiles from the combined filtrates under reduced pressure afforded a viscous yellow/orange oil which was redissolved in a minimal amount of 1:1 ether/$CH_2Cl_2$ and chromatographed on $SiO_2$ (1'×2"). 10 mL fractions were collected and analyzed by TLC on $SiO_2$ plates developed with 1:1 ether/$CH_2Cl_2$. The column was initially eluted with hexane (50 mL), and then with 1:10 ether/hexane (100 mL) to elute a small quantity of unreacted ($R_P$)-Ph(o-An)(Me)P-$BH_3$. Continued elution with 1:5 ether/hexane (500 mL) afforded a large band containing the product of this Example, and elution with 5:4:1 ether/hexane/$CH_2Cl_2$ (200 mL) afforded a smaller band of an unidentified compound. Several of the fractions containing pure product of Example 23 produced crystals while standing, some of which were set aside. Pure fractions were combined and concentrated by rotary evaporation, affording a light green oily residue. This residue was redissolved in a minimal amount of $CH_2Cl_2$ and 1:1 ether/hexane was added via syringe until the solution became turbid. At this point, several of the previously isolated crystals were added to the mixture, causing formation of a large crop of off-white crystalline product of this Example. The mixture was stored overnight at −20° C. to facilitate further crystallization, and then the greenish mother liquor was removed via cannula and retained in a separate flask. The crystalline product of this Example thus obtained was washed with ether (2×10 mL) and dried thoroughly under reduced pressure. Concentration of the retained mother liquor under reduced pressure, followed by addition of several seed crystals and storage overnight at −20° C. afforded a smaller second crop of crystalline product of this Example. The mother liquor was removed from the crystalline material via cannula, the solid was washed with ether, dried thoroughly under reduced pressure, and combined with the first crop, giving 2.2 g (3.6 mmol, 70% yield) of crystalline product of this Example.

$^1$H NMR ($CDCl_3$): δ8.1–6.7 (m, 27 H, Aryl); δ4.7 (dd, 2H, $J_{HH}$=13.1, $J_{PH}$=10.5 Hz, C$\underline{H}_2$P); δ4.1 (dd, 2 H,$J_{HH}$= 13.5, $J_{PH}$=13.6 Hz, C$\underline{H}_2$P); δ3.5 (s, 6H, OC$\underline{H}_3$); δ1.5–0.4 (br, 6 H, B$\underline{H}_3$). $^{13}$C NMR ($CDCl_3$): δ194.3 (d, $J_{PC}$32 3.5 Hz, $\underline{C}${O}$CH_2$P); δ161.2–110.9 (Aryl); δ55.0 (s, O$\underline{C}H_3$); δ33.0 (d, $J_{PC}$=44.6 Hz; C{O}$\underline{C}H_2$P). $^{31}$P NMR ($CDCl_3$): δ15.4 (br). MS (-FAB): m/z=619.5 (M⁻); 604.5 (M⁻- $BH_3$); 590.5 (M⁻- 2 $BH_3$).

Examples 32 and 33
Deprotection of Phosphine-Boranes from Examples 9 and 10 to Give Chiral, Tridentate Ligands Phosphine-borane from Example 30 (3.4 g, 5.7 mmol) was dissolved in a minimal amount of dry, degassed $CH_2Cl_2$ and dry, degassed $Et_2NH$ (approximately 20 mL) was added via cannula. The reaction flask was then attached to a reflux condenser while purging the system with $N_2$ and the mixture heated to reflux overnight under $N_2$. During this time, a small quantity of a colorless crystalline precipitate formed, presumed to be the oxidized form of Example 32. The slightly yellow mixture was allowed to cool to room temperature and the volatiles were removed under reduced pressure, affording a viscous yellow oily residue. This residue was taken up in dry, degassed ether (20 mL) and the solution filtered through a 3" plug of degassed, basic $Al_2O_3$ via Schlenk frit. The slightly yellow filtrate was collected in a flame-dried Schlenk flask under $N_2$, and removal of the volatiles under reduced pressure afforded pure product of Example 32 (2.2 g, 3.94 mmol 70% yield) as a viscous oil.

Phosphine-borane from Example 31 (0.25 g, 0.40 mmol) was dissolved in a minimal amount of dry, degassed $CH_2Cl_2$ and dry, degassed $Et_3N$ (15 mL) was added via syringe. The resulting solution was transferred via cannula to a separate flask containing degassed $Al_2O_3$, and the mixture stirred overnight at room temperature. The yellow/green supernatant was removed by means of a cannula tipped with filter paper and wrapped with PTFE tape, and collected in a separate flame-dried Schlenk flask under $N_2$. The $Al_2O_3$ was washed with additional degassed 1:1 ether/$CH_2Cl_2$ and the washings removed via cannula-filter and added to the initial filtrate. The filtrate was concentrated to approximately 10 mL under reduced pressure, the yellow/green solution filtered through a 3" plug of basic $Al_2O_3$ via Schlenk frit, and the pale yellow filtrate evaporated under reduced pressure to afford pure product of Example 33 as a viscous pale yellow oil in >90% yield.

32: $^1$H NMR ($CDCl_3$): δ7.6–6.8 (m, 27 H, Aryl); δ3.7 (s, 6H, OC$\underline{H}_3$); δ3.1–2.9 (br m, 4H, C$\underline{H}_2CH_2$P); δ2.7–2.6 (br m, 2H, C$\underline{H}_2CH_2$P); δ2.6–2.5 (br m, 2H, C$H_2$C$\underline{H}_2$P). $^{13}$C NMR ($CDCl_3$): δ161.0 (s, Py$_{para}$); δ160.7 (δ,$J_{PC}$=20 Hz, $\underline{C}$-OC$H_3$); δ137.4–109.9 (Aryl); δ55.0 (s, O$\underline{C}H_3$); δ34.3 (d, $J_{PC}$=18.3 Hz;$\underline{C}H_2CH_2$P); δ25.8 (d, $J_{PC}$=12.4 Hz; $CH_2$ $\underline{C}H_2$P). $^{31}$P NMR ($CDCl_3$): δ−24.8 (s).

33: $^1$H NMR ($CDCl_3$): δ8.1–6.6 (m, 27 H, Aryl); δ4.0 (d, 2H, $J_{HH}$=11.9, C$\underline{H}_2$C{O}); δ3.7 (d, 2 H,$J_{HH}$=11.9, C $\underline{H}_2$C{O}); δ3.4 (s, 6H, OC$\underline{H}_3$). $^{13}$C NMR ($CDCl_3$): δ198.1 (d, $J_{PC}$=30.3 Hz, $\underline{C}${O}$CH_2$P); δ160.6–109.8 (Aryl); δ54.8 (s, O$\underline{C}H_3$); δ36.9 (d, $J_{PC}$=22.3 Hz; C{O}$\underline{C}H_2$P). $^{31}$P NMR ($CDCl_3$): δ−21.5 (s).

Example 34
Enantioselective Allylic Alkylation Reaction

The procedures are exemplified by the experiments carried out with ligand from Example 32 in toluene.

The ligand (from Example 32, 35 µl, 0.251 in toluene, 0.0088 mmol) was dissolved in freshly distilled toluene (1.5 ml ) under a nitrogen atmosphere. To the solution |$Pd_2$ (η$^3$-$C_3H_5$)$_2Cl_2$| (1.45 mg, 0.004 mmol) was added under stirring. After 20 mins, racemic 1,3-diphenyl-l-acetoxypropene (100 mg, 0.40 mmol) was added. Then the solution was cooled to −40OC and allowed to be stirred 30 mins. N,O-bis(trimethylsilyl)acetamide (0.294 ml, 1.2 mmol), dimethyl malonate (0.136 ml, 1.2 mmol) and potassium acetate (2 mg, 0.02 mmol) were added in that order. The reaction was monitored by TLC (eluent: Hexane/ ethylacetate=10/1). After 35 hrs, the solvent was removed in vacuo. Column chromatography on silica gel (eluent: Hexane/ethyl acetate=I 0/1) yielded the pure product (125 mg, 97.2% yield). The optical purity was determined to be 75.2% ee by HPLC (Daicel Chiralcel OD column, 1 ml/min, Hexane/2-Propanol=99/1).

Example 35 (relating to FIG. 6)
α,α'-Dimethyl-o-xylene-α,α'-diol.

A solution of 1,2-diacetylbenzene (18.2 g, 0.112 mol) and isopropanol (18.9 mL, 0.247 mol) in dry dichloromethane (50 mL ) was treated with borane methyl sulfide at −20° C. for 1 hour followed by addition of (S)-Me-CBS (9.8 mL, 11.2 mmol; 1.14M solution in toluene). The reaction mixture was allowed to warm up to 15° C. and stirred overnight. The reaction was quenched by slow addition of water (50 mL). Two phases were separated and the aqueous layer was extracted with dichloromethane (3×50 mL). The combined organic extracts were dried over sodium sulfate and concentrated. The residue was chromatographed on a column of silica gel to give the product (8.87 g, 48%, 90%ee). Recrystallization from dichloromethane-hexane gave a white crystal (100%ee). $^1$H NMR ($CDCl_3$) d 1.51 (d, J 6.5 Hz, 6 H), 2.97 (m, 2 H), 5.15 (q, J 6.5 Hz, 2 H), 7.25 (m, 2 H), 7.40 (m, 2 H); $^{13}$C NMR ($CDCl_3$) d 24.26, 66.85, 125.95, 127.49, 142.04; mass spectrum (EI) 166(M⁺), 148, 133, 105, 77; exact mass calcd for $C_{10}H_{14}O_2O$ 148.0888, found 148.0882.

Example 36 (relating to FIG. 6)
Cyclic Sulfate of α,α'-Dimethyl-o-xylene-α,α'-diol.

To a solution of diol (5.4 g, 32.5 mmol) and triethylamine (18.2 mL, 0.13 mol) in dry dichloromethane (150 mL) was added dropwise a solution of sulfuryl chloride (3.9 mL, 48.7 mmol) at −78° C. during a period of 3.5 h. The mixture was stirred at −78° C. for 45 min and allowed to warm up to 0° C. Stirring was continued overnight. The reaction mixture was diluted with ether (200 mL) and filtered. The filtrate was concentrated and the residue was extracted with hexane (3×70 mL). The combined extracts were passed through a short column of aluminum oxide (neutral, activated)and concentrated, giving a colorless oil (3.66 g, 49%). $^1$H NMR ($CDCl_3$) d 1.93 (d, J 6.7 Hz, 6 H), 5.57 (q, J 6.7 Hz, 2 H), 7.35 (m, 2 H), 7.57 (m, 2 H).

Example 37
General Procedure for Hydrogenation.

In glove-box, a solution of catalyst precursor (0.01 mmol) and phosphine ligand (0.012 mmol) in solvent (10 mL) was stirred for 30 min. The substrate was then added. The reaction mixture was put into a bomb and taken out of the glove-box. The bomb was purged with hydrogen and the reaction was pressurized to a desired initial pressure. Stirring was continued at room temperature for 24–48 h. The reaction mixture was concentrated. For ester substrates, the residue was passed through a short column of silica gel eluting with 50% ethyl acetate in hexane to give the product. For acid substrates, the residue was reacted with excess amount of diazomethane and then treated as ester substrates.

Example 38
General Procedure for Hydrosilylation with the Ruthenium Complexes and Diphenylsilane In a Schlenk tube, a solution of $[RuCl_2(C_6H_6)]_2$ ($4.3\times10^{-3}$ mmol, 0.5 mol%) and ligand (0.189 ml, 0.1M in toluene, 2.2 mol%) in THF (1 mL) was stirred at rt for 10 min, and was treated with AgOTf (4.4 mg, 2 mol %) for 30 min. After the addition of ketone (0.86 mmol), the mixture was cooled to 0° C. and $Ph_2SiH_2$ (0.255 mL, 160 mol%) was added dropwise by a syringe. The temperature was gradually raised to rt. The reaction was monitored by TLC or GC. After the completion of the reaction, methanol (2 mL) was added carefully at 0° C. After gas evolution ceased, the reaction mixture was poured into a solution of hydrochloric acid (1N, 5 mL) at 0° C. The mixture was stirred at 0° C. for 1 hour and extracted with $CH_2Cl_2$ (10 mL×4). The combined organic layers were washed with brine and dried over anhydrous $Na_2SO_4$. The crude product was purified by column chromatography on silica gel. The optical purity of the alcohol products were determined by GC (b-Dex GC Column) or HPLC (Chiracel OD Column).

EXEMPLARY CATALYZED REACTIONS
Asymmetric Hydride Transfer Reaction

The mechanism of hydride transfer reactions in many cases is similar to hydrogenation reactions. The difference between the hydride transfer reaction and hydrogenation is that the hydride transfer process is reversible. The enantioselectivity of hydride transfer reactions may not reflect the degree of enantioselectivity induced by the chiral ligands when the reversed reaction occurs. However, the relative enantioselectivity with different ligands before the equilibrium could be a good indication on inductive effects of these ligands. Transition metal complexes with chiral phosphorus and nitrogen ligands have been used to promote enantioselective hydride-transfer reactions. The enantioselectivity of catalysts for asymmetric reduction of simple ketones such as acetophenone were compared to those of the tridentate ligands of the present invention and known $C_2$ symmetric bidentate chiral phosphines. Group VIII transition metal complexes with chelating bidentate diphosphines like Diop, Chiraphos, Norphos and BINAP have been used in asymmetric reduction of acetophenone by propan-2-ol. The enantioselectivities in the range from 1.5 to 24% ee have been achieved with low conversion (20 to 60%). Using $RuCl_2$ ($C_6H_6$) as precursor bearing tridentate ligand A (compound 5) (Table I, below), up to 50%ee has been obtained with excellent conversion (>95). Although the enantioselectivity in this system is moderate, the hydride-transfer reactions with these tridentate ligands are more effective than with known chiral bidentate phosphines.

TABLE I

Asymmetric Hydride Transfer Reaction

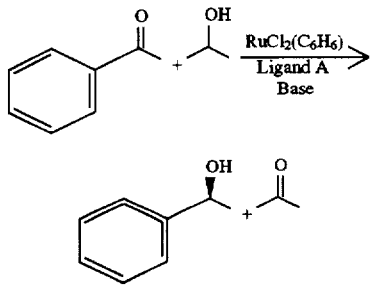

| [Ru]$^{2+}$ (1 mol %) | L* (1 equiv.) | Base | Base equiv. | Yield (%) | ee (%) |
|---|---|---|---|---|---|
| RuCl$_2$ (C$_6$H$_6$) | Ligand A | KOH | 5 | 96 | 17 |
| RuCl$_2$ (C$_6$H$_6$) | Ligand A | NaOH | 5 | 93 | 28 |
| RuCl$_2$ (C$_6$H$_6$) | Ligand A | NaOH | 125 | 93 | 39 |
| RuCl$_2$ (C$_6$H$_6$) | Ligand A | NaH | 10 | 94 | 40 |
| RuCl$_2$ (C$_6$H$_6$) | Ligand A | NaOCH$_3$ | 5 | 90 | 50 |

Asymmetric Hydrogenation

While a variety of functionalized ketones, imines and olefins have been hydrogenated with mainly RU(II) and Rh(I) catalysts to produce optically active alcohols, amines and alkanes in very high enantiomeric excesses (ee's), the corresponding enantioselective hydrogenation of ketones, in-ines and olefins without a secondary ligating functionality often gives moderate enantioselectivity with few exceptions. In contrast to the situation with group VIII transition metal catalysts, however, high enantioselectivities (>90% ee) by using various stoichiometric chiral reducing agents (mainly Al and B compounds) have been achieved in the reduction of unfunctionalized ketones and imines. These reagents have been used in the synthesis of various optically pure pharmaceuticals such as prostaglandins and fluoxetine hydrochloride (Prozac). Recently, high enantioselectivity has been obtained using chiral oxazaborolidines to catalyze the enantioselective reduction of unfunctionalized ketones and imines. These reactions, however, suffer the disadvantages of requiring either a stoichiometric amount of reducing agents or of low catalytic turnover numbers. To develop a more effective method, transition metal catalysts for enantioselective hydrogenation are more desirable because they give very high turnovers. This invention uses the aforementioned chiral tridentate ligands to enforce strong non-bonding interactions between the catalyst and the substrate. Using rhodium as the transition metal and an unfunctionalized ketone as a substrate, FIG. 7 shows a reasonable reaction pathway for asymmetric hydrogenation with a cationic rhodium complex. Oxidative addition of $H_2$ and substrate binding to a square planar rhodium catalyst generates a key intermediate in which the binding geometry of the prochiral ketone is dictated by the chiral ligand. After migratory insertion and reductive elimination steps, optically active alcohols can be generated. In a related fashion, a neutral rhodium (I) complex (RhHL, L=chiral tridentate ligand) can be used as a catalyst as it too is active in the asymmetric hydrogenation of ketones. Alternatively, any of the transition metals may be substituted for rhodium if they demonstrate enhanced selectivity in a particular process. For example, $RuH_2(H_2)(PPh_3)_3$ has been used as an effective catalyst for hydrogenation of simple ketones and sometimes esters can also be reduced to corresponding alcohols. The three phosphine groups bind with ruthenium in the whole catalytic process. Replacing these three phosphine groups with tridentate ligands (one nitrogen and two phosphines), ruthenium complexes are active for hydrogenation of simple ketones and many other substrates. Asymmetric hydrogenation of dehydroamnino acids has been done. The results are shown in Table II.

Asymmetric Hydrosilylation

Asymmetric hydrosilylation of ketones and imines produce silyl ethers and silyl amines, which can be hydrolyzed to give the corresponding alcohols and amines. Asymmetric hydrosilylation of olefins generates silyl alkanes. Group VIII transition metals are effective catalysts for hydrosilylation. For example, rhodium complexes such as Wilkinson catalyst $RhCl(PPh_3)_3$ show great activities toward hydrosilylation of ketones. Many chiral bidentate phosphines have been used for the asymmetric hydrosilylation reaction and moderate enantioselectivities (50–85%ee) have been obtained. Recently, chiral nitrogen ligands containing a pyridine skeleton (e.g., bidentate Pythia and tridentate Pybox (a trinitrogen ligand) have been successfully used in the asymmetric reactions (95–99%ee). With bidentate chiral Pythia ligands, more than 10 fold excesses of ligands is needed for achieving high enantioselectivity. The rationale of this phenomena is that three coordinated nitrogens are required for effective asymmetric induction in the Rh system. This observation was further verified with a Rh catalyst bearing a chiral tridentate ligand [bis(oxazolinyl)pyridine—Pybox]. In this system, an equimolar amount of the nitrogen ligand with respect to rhodium metal gives excellent enantioselectivity for the asymmetric hydrosilylation of ketones. This exemplifies how a tridentate ligand can be more desirable for individual asymmetric reactions. This invention discloses chiral tridentate ligands containing both a pyridine and two phosphines. These ligands can have advantages over known bidentate phosphine ligands and tridentate nitrogen ligands. They have a similar geometry as tridentate nitrogen ligands and the catalysts with the tridentate ligands of the present invention have high catalytic activities similar to known bidentate phosphine ligands. Table III shows the results of asymmetric hydrosilylation catalyzed via a ligand of the present invention. Asymmetric hydrosilylation has been tested using several different tridentate ligand systems. The present inventors have surprisingly found that ruthenium compounds exhibit excellent catalytic activities. Ruthenium catalysts are less expensive than rhodium complexes, and accordingly have broad applicability. As shown in Table III, ruthenium complexes bearing tridentate ligands of the present invention, containing more than one phosphine, are active for the hydrosilylation reaction, whereas ruthenium complexes with Pybox (three nitrogen) ligands do not have good catalytic activity or selectivity.

Asymmetric hydroformylation

Asymmetric hydroformylation provides a potentially versatile method for the preparation of enantiomerically pure aldehydes which are useful as precursors of many biologically active compounds. Despite extensive investigations, efficient hydroformylation catalysts with excellent control of both regiochemistry (branched/normal) and absolute stereochemistry have not been realized. So far, the most notable advances in this area are hydroformylation of arylethenes catalyzed by chiral diphosphine-$PtCl_2$—$SnCl_2$ species or by chiral phosphinephosphite-Rh(I) complexes. To design an effective asymmetric hydroformylation catalyst, this invention uses rhodium and other group VIII complexes as catalysts because they have high activities for hydroformylation reaction. One frequently used catalyst for hydroformylation is $RhH(CO)_2(PPh_3)_2$. During the catalytic process, two phosphines and one CO stay bound with Rh during insertion of coordinated olefin into the metal hydride, the migratory insertion of the CO ligand, and oxidative addition of $H_2$ and reductive elimination of aldehyde. This reaction may form branched and/or normal chain aldehydes, depending on the nature of the metal catalyst, the olefin substitution pattern and the coordination environment. Chiral tridentate ligands can be used in substitution of two phosphine and one CO ligands. Group VIII transition metal complexes bearing tridentate ligands can achieve good activity for hydroformylation, as the coordination environment differs dramatically from rhodium complexes with known chiral bidentate phosphines. As in the aforementioned discussion on asymmetric hydrogenation, chiral tridentate ligands modify the coordination environment by bring the chirality closer to the bond forming process.

Asymmetric Allylic Alkylation

Allylic alkylation catalyzed by Pd complexes is an extremely versatile carbon-carbon bond forming method. Asymmetric allylic alkylation has received considerable attention and excellent enantioselectivities have been achieved in some cases with chiral bidentate phosphine, nitrogen and phosphine-nitrogen ligand systems. In order to achieve substrate generality, the search for efficient ligand systems is required. This invention addresses the ligand design principle by understanding the nature of the reaction. Unlike many asymmetric reactions in which the creation of stereogenic centers occurs with the coordination sphere of metal, metal catalyzed allylic alkylation generally involve bond-breaking and bond-forming steps outside the coordination sphere of the metals. A particularly intriguing idea in the literature is to create a deep chiral pocket surrounding the substrate. For chiral bidentate ligands, these deep chiral pockets are generated by increasing the bite angle of chelating phosphines. As the P—Pd—P bite angle increases, the diarylphosphine units are pushed toward embracing the substrate and thus enhance the chiral recognition. This idea has successfully lead to efficient chiral bidentate phosphines for asymmetric allylic alkylation. The present invention employed the tridentate ligands disclosed herein for the catalytic study. Compared with many bidentate phosphines, tridentate ligands with two phosphines in trans positions can create a deeper chiral pocket because the bite angle of P—Pd—P is about 180°. A profound chiral pocket is formed by incorporating the Pd metal into a tridentate ligand of the present invention. High enantioselectivities (up to 75% ee) and excellent conversion (up to 100%) have been obtained with one of the chiral tridentate ligands of the present invention (Table IV). This is the first time that Pd-catalyzed allylic alkylation has been carried out in a tridentate ligand system.

Asymmetric Cyclopropanation

Reaction between a diazo compound and an alkene to form cyclopropanes is a fundamental organic reaction. Many transition metals (e.g., Cu, Rh, Ru, and Co) can facilitate this reaction and asymmetric cyclopropanation has been achieved. A variety of chiral ligands ranging from amino acids, Salen Schiff bases to semicorrins and bisoxazolines were employed in this reaction. Excellent enantioselectivities (>99% ee) have been obtained in many cases. However, the trans/cis selectivity in cyclopropanation is difficult to control by the chiral ligands. This invention provides efficient asymmetric cyclopropanation catalysts which could give high enantioselectivity and excellent diastereoselectivity.

Compared to bidentate bisoxazoline ligands, the tridentate ligands of the present invention have a larger bite angle for P—Ru—P (about 180°). The substituents on phosphines form a well defined deep chiral cavity. For example, the two equatorial phenyl groups in some tridentate ligands move out of P—Ru—P line and could serve as effective blocking groups. Since a pyridine nitrogen is in the trans position of carbene, it provides the right electronic properties for the cyclopropanation reaction. The two trans phosphines are steric control elements for the asymmetric reaction. This unique chiral environment is attractive for the asymmetric cyclopropanation reaction.

Figure 11:
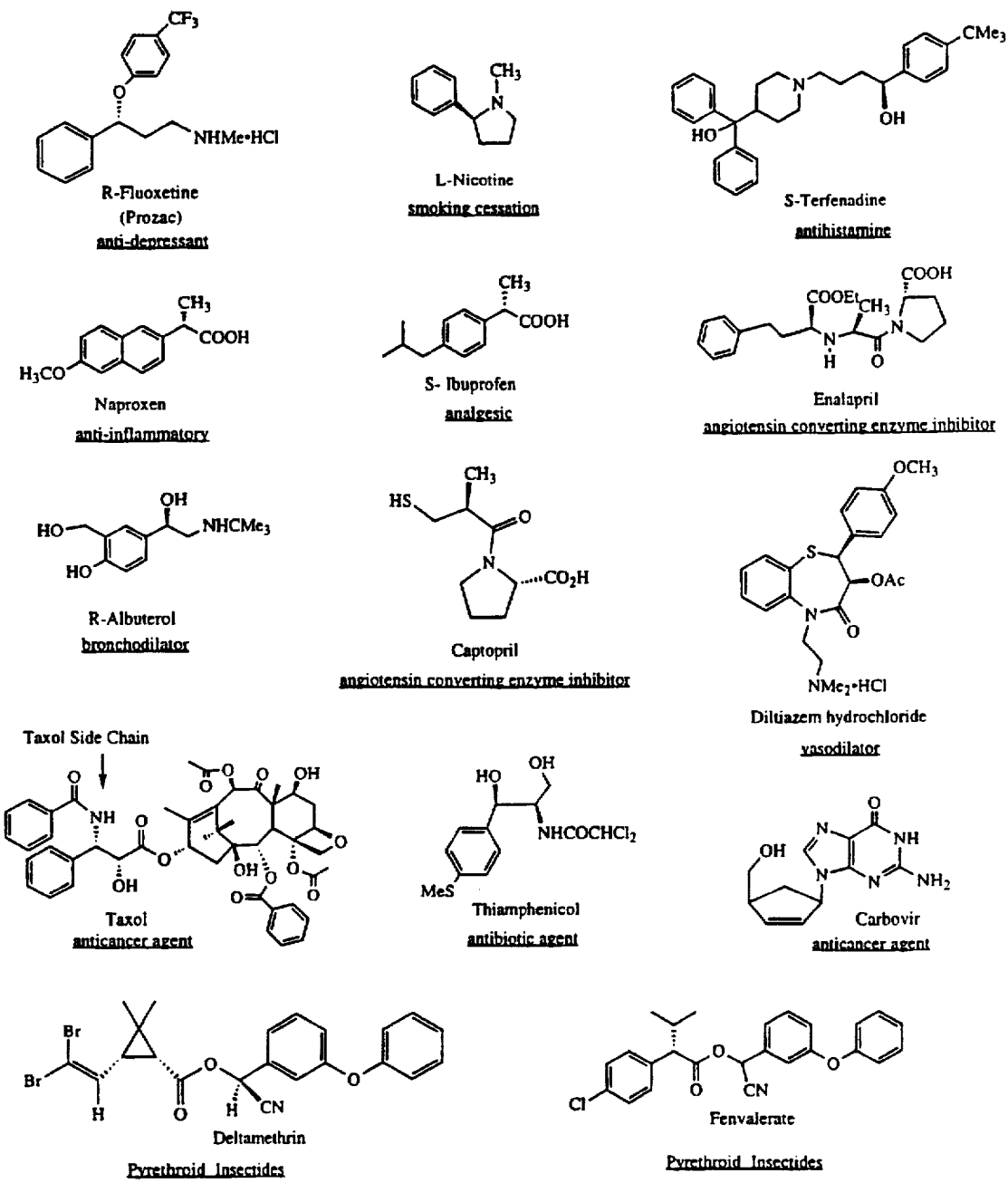
FIG. 11 depicts various target drugs and agrochemicals to be synthesized by means of catalysts of the present invention.

FIG. 11 lists several potential chiral drugs and agrochemicals which could be synthesized through asymmetric methodologies disclosed in this invention.

TABLES

Asymmetric Synthesis Catalyzed by Transition Metal Complexes with New Chiral Ligands

TABLE I

Asymmetric Hydride Transfer Reaction

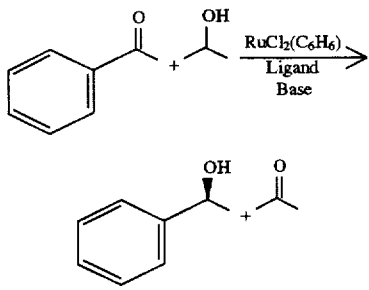

| [Ru]$^{2+}$ (1 mol %) | L* (1 equiv.) | Base | Base equiv. | Yield (%) | ee (%) |
|---|---|---|---|---|---|
| RuCl$_2$ (C$_6$H$_6$) | Ligand | KOH | 5 | 96 | 17 |
| RuCl$_2$ (C$_6$H$_6$) | Ligand | NaOH | 5 | 93 | 28 |
| RuCl$_2$ (C$_6$H$_6$) | Ligand | NaOH | 125 | 93 | 39 |
| RuCl$_2$ (C$_6$H$_6$) | Ligand | NaH | 10 | 94 | 40 |
| RuCl$_2$ (C$_6$H$_6$) | Ligand | NaOCH$_3$ | 5 | 90 | 50 |

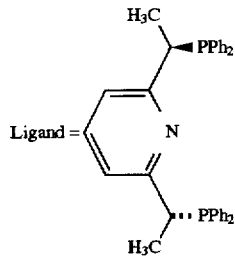

Syntheses and Application of Chiral Tridentate Ligands

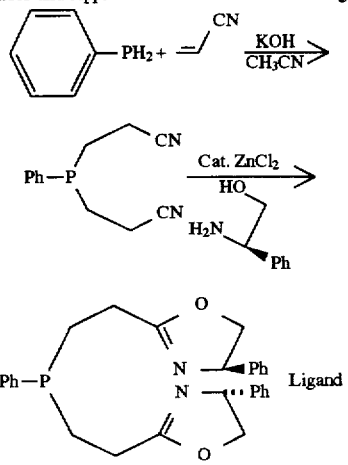

TABLE I-continued $$R_1 \underset{O}{\overset{}{\|}} R_2 + CH_3 \underset{OH}{\overset{}{\|}} CH_3 \xrightarrow[NaH]{[RuCl_2(C_6H_6)]_2 \text{ Ligand}} R_1 \underset{OH}{\overset{}{\|}} R_2 + CH_3 \underset{O}{\overset{}{\|}} CH_3$$

| Substrate | Temp (°C.) | Time (h) | Yield (%) | ee (%) |
|---|---|---|---|---|
| acetophenone | 80 | 0.2 | 96 | 80 (R) |
| 2-acetonaphthone | 80 | 1 | 93 | 73 (R) |
| 1-acetonaphthone | 80 | 0.3 | 81 | 76 (R) |
| pinacolone | 25 | 12 | 93 | 90 (R) |

TABLE II

Asymmetric Hydrogenations of Dehydroamino Acid Derivatives $$R \diagup\!\!\!\diagdown \overset{COOH}{\underset{NHCOR'}{}} + H_2 \text{ (1 atm)} \xrightarrow[EtOH, rt, 24 h]{[Rh(COD)_2]BF_4 (1 \text{ mol } \%) \text{ Ligand (1.1 mol \%), Et}_3N(50 \text{ mol }\%)} R \diagup\!\!\!\diagdown \overset{COOH}{\underset{NHCOR'}{}} \text{ (S)}$$

| Substrate | Ligand | % ee[a] | Ligand | % ee[a] |
|---|---|---|---|---|
| CH₂=C(COOH)NHCOCH₃ | Benphos | 33.5 | Trans-Phos | 5.5 |
| PhCH=C(COOH)NHCOCH₃ | Benphos | 72.2 | Trans-Phos | 68.4 |
| PhCH=C(COOH)NHCOPh | Benphos | 67.1 | Trans-Phos | 74.2 |

[a] % ee determined by GC using Chirasil-VAL III FSOT Column of the corresponding methyl ester.

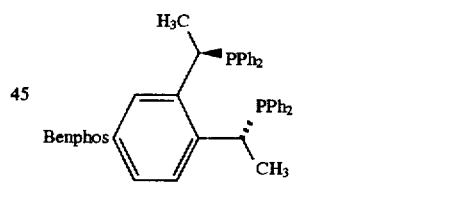

Benphos

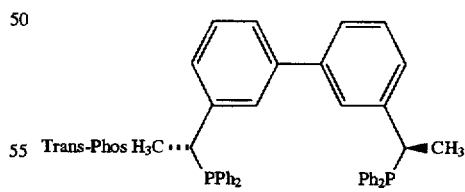

Trans-Phos

TABLE III
Asymmetric Hydrosilylation
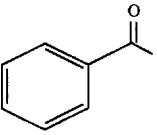
| Substrate | Ligand | Yield (%) | ee (%) |
|---|---|---|---|
| 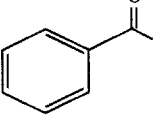 | 1 | 90 | 67 |
| 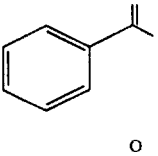 | 2 | 98 | 54 |
| 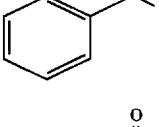 | 3 | 55 | 75 |
| 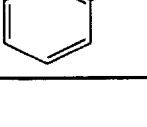 | 4 | 15 | 0 |
| 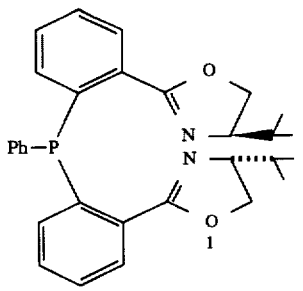 | 5 | 100 | 5 |
TABLE III-continued
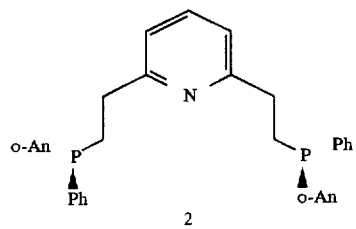
2
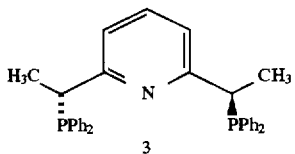
3
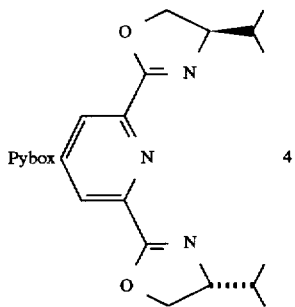
Pybox  4
BINAP 5

TABLE IV

Asymmetric Allylic Alkylation

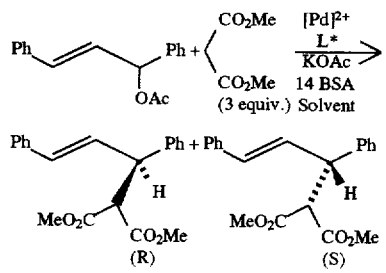

| [Pd]$^{2+}$ (1 mol %) | L* (2.2 equiv.) | KOAc (mol %) | Solvent | Yield (%) | ee (%) |
|---|---|---|---|---|---|
| ($\eta^3$-Allyl)PdCl | Ligand | 5 | CH$_2$Cl$_2$ | 93.3 | 60.8 |
| ($\eta^3$-Allyl)PdCl | Ligand | 5 | THF | 97.2 | 56.6 |
| ($\eta^3$-Allyl)PdCl | Ligand | — | CH$_2$Cl$_2$ | 93.3 | 55.2 |
| ($\eta^3$-Allyl)PdCl | Ligand | 5 | Benzene | 99.1 | 66.2 |
| Pd(OAc)$_2$ | Ligand | 5 | CH$_2$Cl$_2$ | 93.3 | 56.9 |
| ($\eta^3$-Allyl)PdCl | Ligand | 5 | Toluene (−40° C.) | 99.5 | 75.2 |

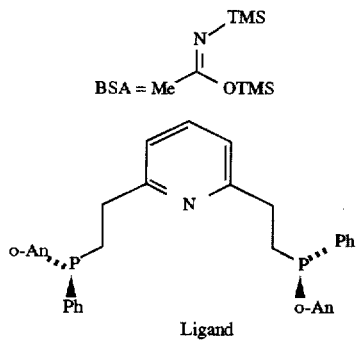

What is claimed is:

1. A composition comprising about 90% to 100% of a first enantiomeric configuration of a chiral ligand and about 10% to 0% of at least one enantiomeric configuration of said chiral ligand different from said first enantiomeric configuration, said ligand having the following structure:

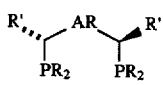

wherein AR is any aromatic or ring structure, and R is selected from the group consisting of aryl, alkyl, aralkyl, ring-substituted aralkyl substituted aryl and combinations thereof.

2. The composition of claim 1, wherein said ligand can be any one structure selected from the group consisting of:

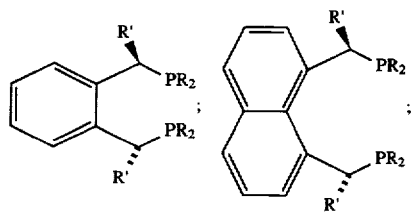

-continued

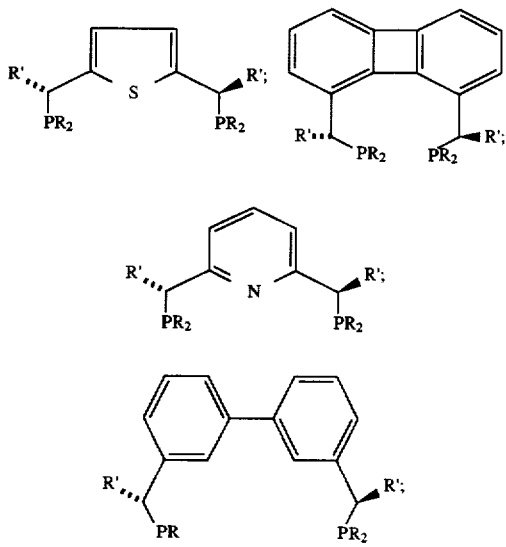

-continued

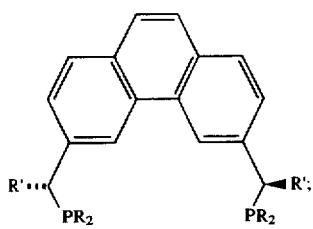

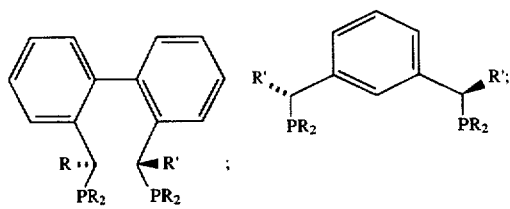

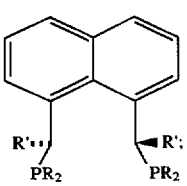

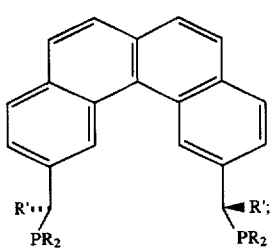

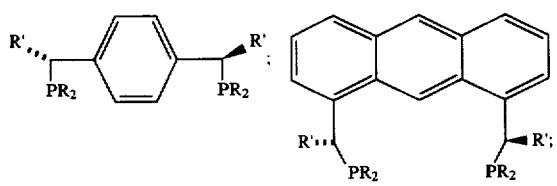

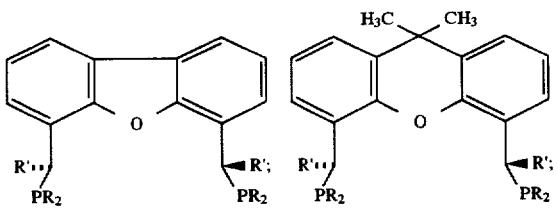

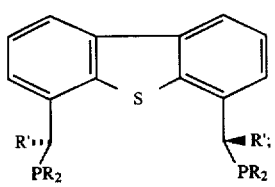

wherein Me is $CH_3$ and n is NH.

3. The composition of claim 1, wherein said ligand further comprises substituents bonded to said AR group which are selected from the group consisting of: $N(CH_3)_2$, $OCH_3$, $CH_3$, hydrogen, fluorine, chlorine, bromine and $NO_2$.

4. A catalyst which comprises:
   a transition metal; and
   a composition comprising about 90% to 100% of a first enantiomeric configuration of a chiral ligand and about 10% to 0% of at least one enantiomeric configuration of said chiral ligand different from said first enantiomeric configuration, said ligand having the following structure:

wherein AR is any aromatic or ring structure, and R is selected from the group consisting of aryl, alkyl, aralkyl, ring-substituted aralkyl, substituted aryl and combinations thereof.

5. The catalyst of claim 4, wherein said ligand can be any one structure selected from the group consisting of:

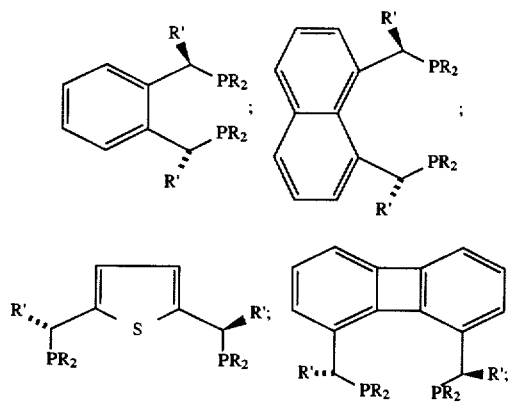
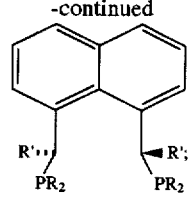
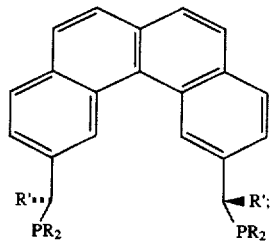
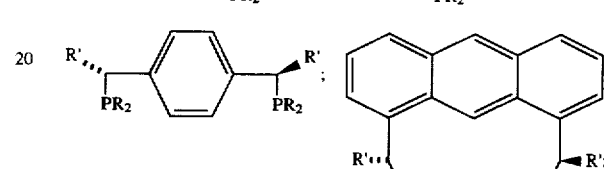
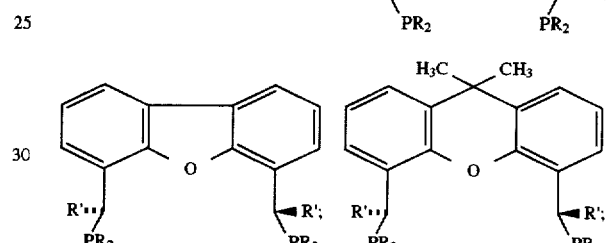
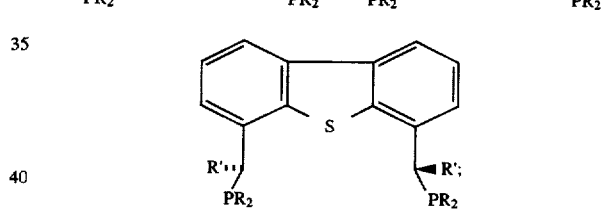
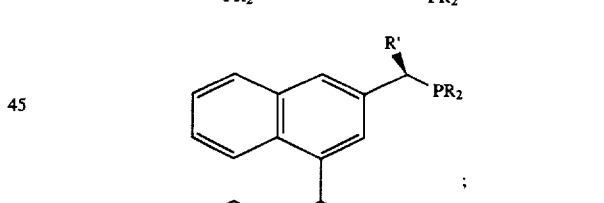
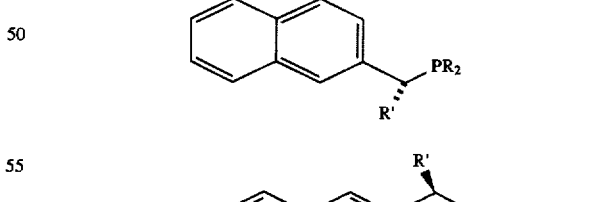
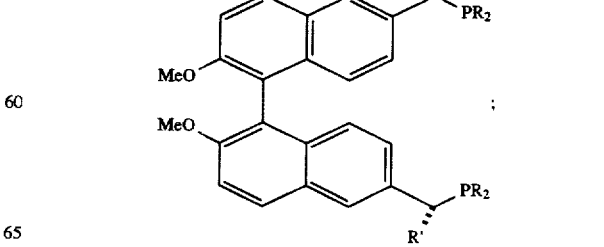

47

-continued

[Chemical structures showing various ligands with R', PR2, O, CH3, S, OCH3, and CH3O substituents on aromatic rings]

and

[Chemical structure showing biphenyl with multiple OCH3, CH3O, PR2, and R' substituents]

wherein Me is CH₃ and n is NH.

6. The catalyst of claim 4, further comprising substituents bonded to said AR group which are selected from the group consisting of: $N(CH_3)_2$, $OCH_3$, $CH_3$, hydrogen, fluorine, chlorine, bromine and $NO_2$.

7. The catalyst of claim 4, wherein said transition metal is at least one metal selected from Group VIII metals.

8. The catalyst of claim 7, wherein said Group VIII metal is selected from the group consisting of rhodium, iridium, ruthenium and palladium.

9. A composition comprising about 90% to 100% of a first enantiomeric configuration of a chiral ligand and about 10% to 0% of at least one enantiomeric configuration of said chiral ligand different from said first enantiomeric configuration, said ligand having two chiral phosphine groups in transpositions and an aromatic backbone.

10. The composition of claim 1, wherein said ligand is tridentate.

11. The composition of claim 1, wherein said ligand is bidentate.

12. The composition of claim 11, wherein said ligand further comprises a pyridine nitrogen atom.

13. The composition of claim 12, wherein said pyridine nitrogen atom is located on said AR between said two PR₂ groups.

14. The composition of claim 1, wherein said AR is inflexible.

15. The composition of claim 14, wherein said ligand is bidentate.

16. The composition of claim 14, wherein said ligand is tridentate.

17. The composition of claim 4, wherein said ligand binds said transition metal complex in a planar geometry.

18. The composition of claim 9, wherein said phosphine groups are selected from the group consisting of alkyl phosphines, arylphosphines and phosphites.

19. The composition of claim 1, wherein said ligand is prepared by asymmetric reduction with chiral borane reducing agents.

20. The composition of claim 12, wherein a bite angle defined by said phosphine groups and said pyridine nitrogen atom is from approximately 80° to approximately 180°.

21. The composition of claim 4, wherein said catalyst provides a reaction conversion rate of about 100%.

22. The composition of claim 12, wherein a pyridine ring containing said pyridine nitrogen atom further comprises at least one substituent selected from the group consisting of $NMe_2$, OMe, Me, H, F, Cl, Br, and $NO_2$.

23. The composition of claim 1, wherein at least one of said PR₂ groups further includes substituents selected from the group consisting of Me, Et, Pr, Bu, Ph, O-Aryl, O-Alkyl and O-AR.

24. A composition comprising about 90% to 100% of a first enantiomeric configuration of a chiral ligand and about 10% to 0% of at least one enantiomeric configuration of said chiral ligand different from said first enantiomeric configuration, said ligand having the following structure:

[Chemical structure showing AR with two (CH₂)n chains connecting to P atoms with R₁ and R₂ substituents]

wherein AR is any aromatic or ring structure, R₁ and R₂ are different and are selected from the group consisting of aryl, alkyl, aralkyl, ring-substituted aralkyl, substituted aryl and combinations thereof, and n=1 or 2.

25. A chiral ligand having the following structure:

[Chemical structure showing AR with two R' and PR₂ substituents]

wherein AR is any aromatic or ring structure, and R is selected from the group consisting of aryl, alkyl, aralkyl, ring-substituted aralkyl, substituted aryl and combinations thereof, wherein said ligand is bidentate and further comprises a pyridine nitrogen atom.

26. The chiral ligand of claim 25, wherein said pyridine nitrogen atom is located on said AR between said two PR₂ groups.

27. The chiral ligand of claim 25, wherein a bite angle defined by said phosphine groups and said pyridine nitrogen atom is from approximately 80° to approximately 180°.

28. The chiral ligand of claim 25, wherein a pyridine ring containing said pyridine nitrogen atom further comprises at least one substituent selected from the group consisting of $NMe_2$, OMe, Me, H, F, Cl, Br, and $NO_2$.

29. A chiral ligand having the following structure:

[Chemical structure showing AR with two R' and PR₂ substituents]

wherein AR is any aromatic or ring structure, and R is selected from the group consisting of aryl, alkyl, aralkyl, ring-substituted aralkyl, substituted aryl and combinations thereof, and wherein said ligand is prepared by asymmetric reduction with chiral borane reducing agents.

30. The composition of claim 1, wherein said composition is made by a process comprising:

synthesizing chiral scalemic phosphine; and coupling said scalemic phosphine with a pyridine.

31. The composition of claim 9, wherein said composition is made by a process comprising asymmetric reduction with chiral borane reducing agents.

32. The composition of claim 9, wherein said composition is made by a process comprising:

synthesizing chiral scalemic phosphine; and coupling said scalemic phosphine with a pyridine.

33. The composition of claim 24, wherein said composition is made by a process comprising asymmetric reduction with chiral borane reducing agents.

34. The composition of claim 24, wherein said composition is made by a process comprising:

synthesizing chiral scalemic phosphine; and coupling said scalemic phosphine with a pyridine.

35. The chiral ligand of claim 25, wherein said chiral ligand is made by a process comprising:

synthesizing chiral scalemic phosphine; and coupling said scalemic phosphine with a pyridine.

* * * * *